(12) United States Patent  
Koerner et al.

(10) Patent No.: US 9,772,275 B2  
(45) Date of Patent: Sep. 26, 2017

(54) METHOD AND APPARATUS FOR OPTICAL ABSORPTION MEASUREMENTS

(71) Applicant: Universität Stuttgart, Stuttgart (DE)

(72) Inventors: Klaus Koerner, Stuttgart (DE); Christof Pruss, Ostfildern (DE); Alois Herkommer, Aalen (DE); Wolfgang Osten, Stuttgart (DE); Daniel Claus, Stuttgart (DE)

(73) Assignee: Universität Stuttgart, Stuttgart (DE)

( * ) Notice: Subject to any disclaimer, the term of this patent is extended or adjusted under 35 U.S.C. 154(b) by 0 days.

(21) Appl. No.: 14/840,728

(22) Filed: Aug. 31, 2015

(65) Prior Publication Data

US 2016/0076997 A1   Mar. 17, 2016

(30) Foreign Application Priority Data

Sep. 17, 2014   (EP) .................................... 14003225

(51) Int. Cl.
*G01N 21/35*   (2014.01)
*A61B 10/02*   (2006.01)
*A61B 5/00*   (2006.01)

(52) U.S. Cl.
CPC .......... *G01N 21/35* (2013.01); *A61B 5/0086* (2013.01); *A61B 5/6848* (2013.01); *A61B 10/0266* (2013.01); *G01N 2201/06113* (2013.01)

(58) Field of Classification Search
CPC .................................................... G01N 21/35
See application file for complete search history.

(56) References Cited

U.S. PATENT DOCUMENTS 4,383,762 A   5/1983   Burkert
5,309,217 A   5/1994   Simon et al.
(Continued)

FOREIGN PATENT DOCUMENTS

DE   30 05 520 A1   8/1981
DE   210 973 A1   6/1984
(Continued)

OTHER PUBLICATIONS

Nallala, Jayakrupakar et al.: "Infrared Imaging as a Cancer Diagnostic Tool: Introducing a New Concept of Spectral Barcodes for Identifying Molecular Changes in Colon Tumors" In: Cytrometry Part A, 83A, pp. 294-300, 2013
(Continued)

*Primary Examiner* — David Porta
*Assistant Examiner* — Hugh H Maupin
(74) *Attorney, Agent, or Firm* — Banner & Witcoff, Ltd.

(57) ABSTRACT

Disclosed herein is a measuring probe and an arrangement for measuring spectral absorption, preferably in the infrared. Furthermore, the invention relates to a method for spectroscopically measuring absorption. The measuring probe may comprise a cutting apparatus configured to cut a slice or respectively flap off of a sample to be measured; a measuring gap configured to accommodate the sample slice; an optical window element for coupling measuring light into, or respectively out of the measuring gap; and an end reflector designed and arranged to reflect the measuring light propagated through the measuring gap back into the measuring gap. The arrangement for measuring spectral absorption may comprise the measuring probe, a light source and an apparatus for the spectral analysis of the measuring light coupled out of the measuring gap.

20 Claims, 23 Drawing Sheets

(56) References Cited

U.S. PATENT DOCUMENTS

| | | | |
|---|---|---|---|
| 7,697,976 B2 | 4/2010 | Wu et al. | |
| 8,452,356 B2 | 5/2013 | Vestel et al. | |
| 8,593,630 B2 | 11/2013 | Bhargava et al. | |
| 2005/0203419 A1* | 9/2005 | Ramanujam et al. | 600/473 |
| 2008/0241866 A1* | 10/2008 | Korlach | G01N 21/6452 435/8 |
| 2009/0326385 A1* | 12/2009 | Hendriks | A61B 5/0066 600/478 |
| 2010/0081928 A1* | 4/2010 | Hyde et al. | 600/431 |
| 2014/0228661 A1 | 8/2014 | Popa-Simil et al. | |

FOREIGN PATENT DOCUMENTS

| | | |
|---|---|---|
| DE | 34 00 389 A1 | 7/1985 |
| DE | 42 12 143 A1 | 11/1992 |
| DE | 10 2014 002 514 A1 | 8/2015 |
| GB | 2 154 019 B | 1/1988 |
| WO | 2014/068468 A1 | 5/2014 |

OTHER PUBLICATIONS

Nallala, Jayakrupakar et al.: "Novel concepts in infrared spectral imaging as a cancer diagnostic tool" In: SpectroscopyEurope vol. 25, No. 6, 2013.

Bellisola, Giuseppe et al.: "Infrared spectroscopy and microscopy in cancer research and diagnosis" In: Am. J. Cancer Res. 2012: 2(1), pp. 1-21.

Lee, So Yeong et al.: "Infrared spectroscopy characterization of normal and lung cancer cells originated from epithelium" In: Journal of Veterinary Science 2009: 10 (4), pp. 299-304.

Wood, B. R. et al.: "Progress in Fourier Transform Infrared Spectroscopic Imaging Applied to Venereal Cancer Diagnosis" In: Veterinary Pathology Online: http://vet.sagepub.com/content/early/2013/09/05/0300985813501340, Sep. 5, 2013.

Hughes, Caryn Siân: "Development of Fourier Transform Infrared Spectroscopy for Drug Response Analysis" Thesis submitted to the University of Manchester (School of Chemical Engineering and Analytical Science) for the degree of Doctor of Philosophy in the Faculty of Engineering and Physical Sciences, 2011.

Venkatachalam, P. et al.: "Diagnosis of Breast Cancer Based on FT-IR Spectroscopy" In: Perspectives in Vibrational Spectroscopy: ICOPVS 2008, American Institute of Physics, ISBN 978-0-7354-0606-3, pp. 144-148.

Shaw, R. Anthony et al.: "Infrared Spectroscopy in Clinical and Diagnostic Analysis" In: Encyclopedia of Analytical Chemistry, John Wiley & Sons Ltd, Chichester, ISBN 0471 97670 9, pp. 1-20, 2000.

Matsuura, Yuji et al.: "Hollow-fiber-based flexible probe for remote measurement of infrared attenuated total reflection" In: Applied Optics, vol. 48, No. 28 (2009), pp. 5396-5400.

Körner, K.: "Ein neues Interferometer für die Fourier-Spektroskopie" In: Optik, vol. 68, pp. 217-223 (1984).

* cited by examiner

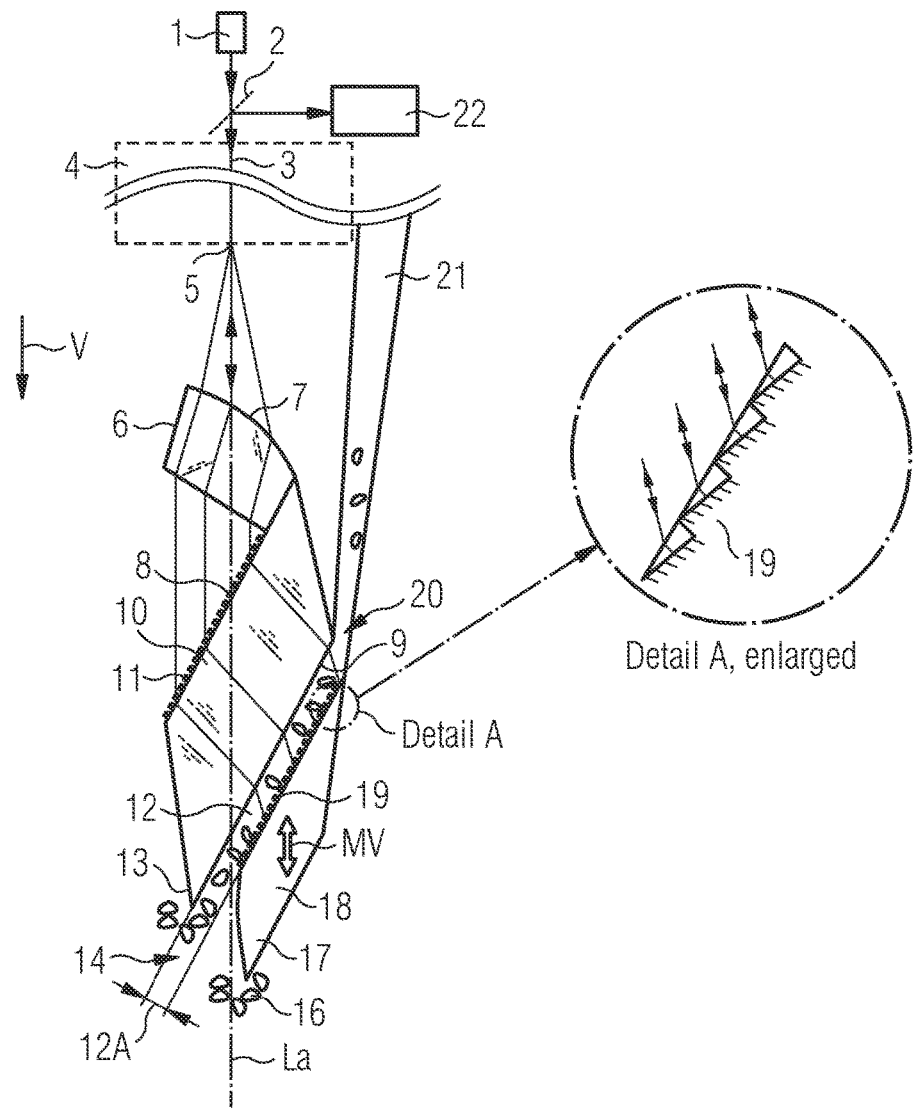

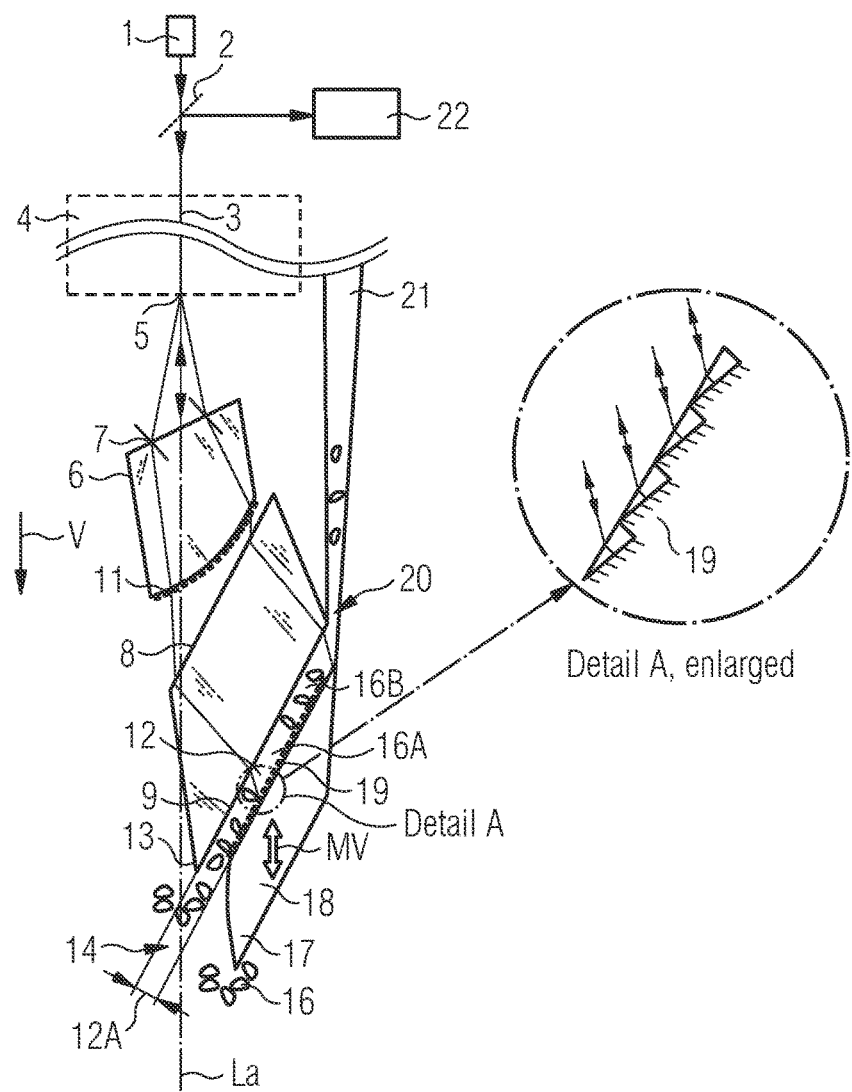

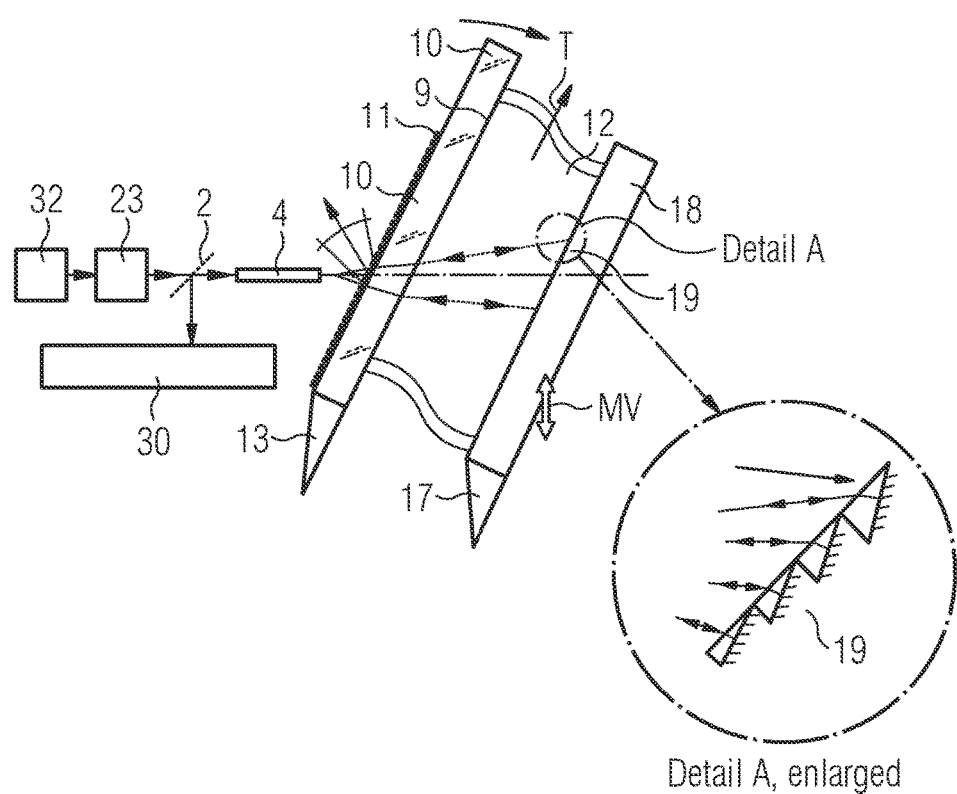

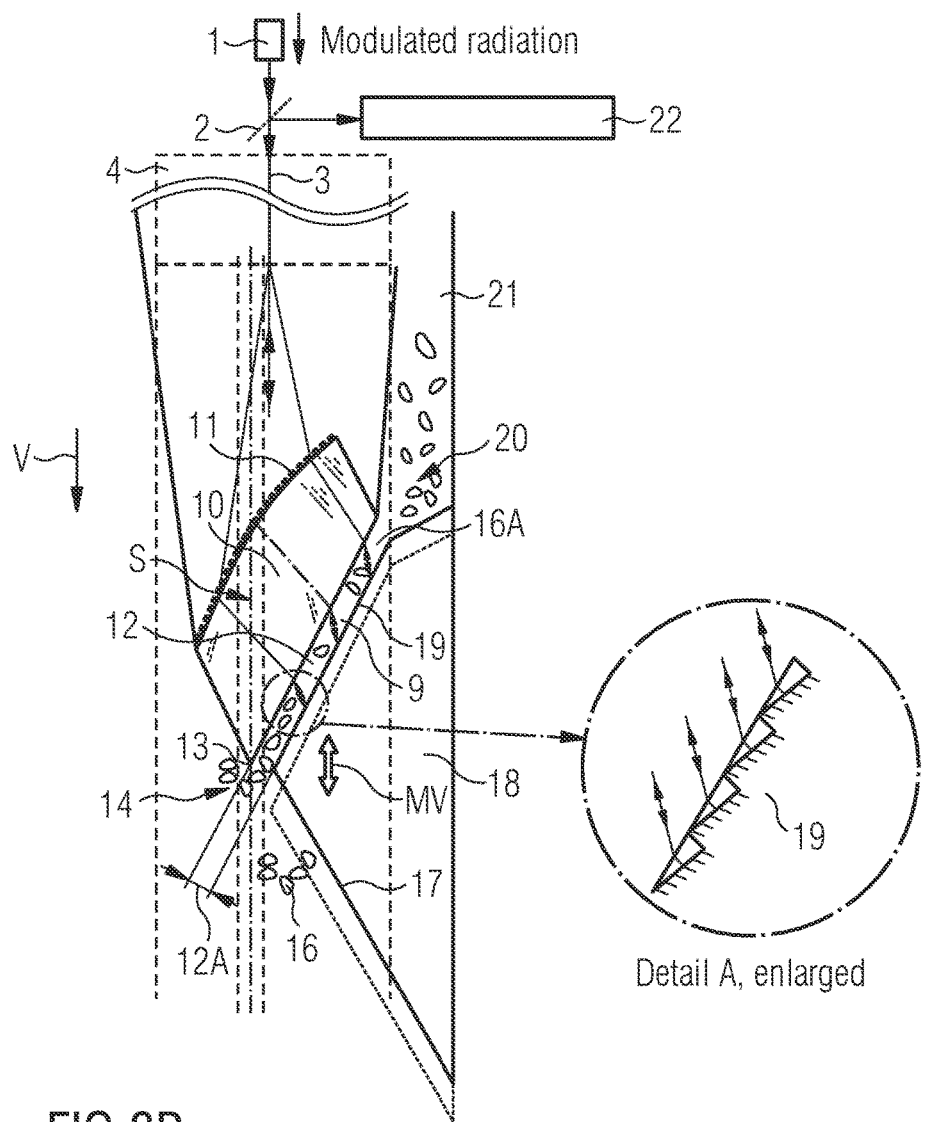
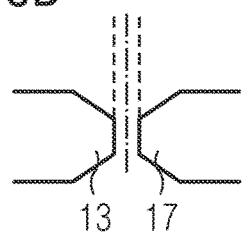

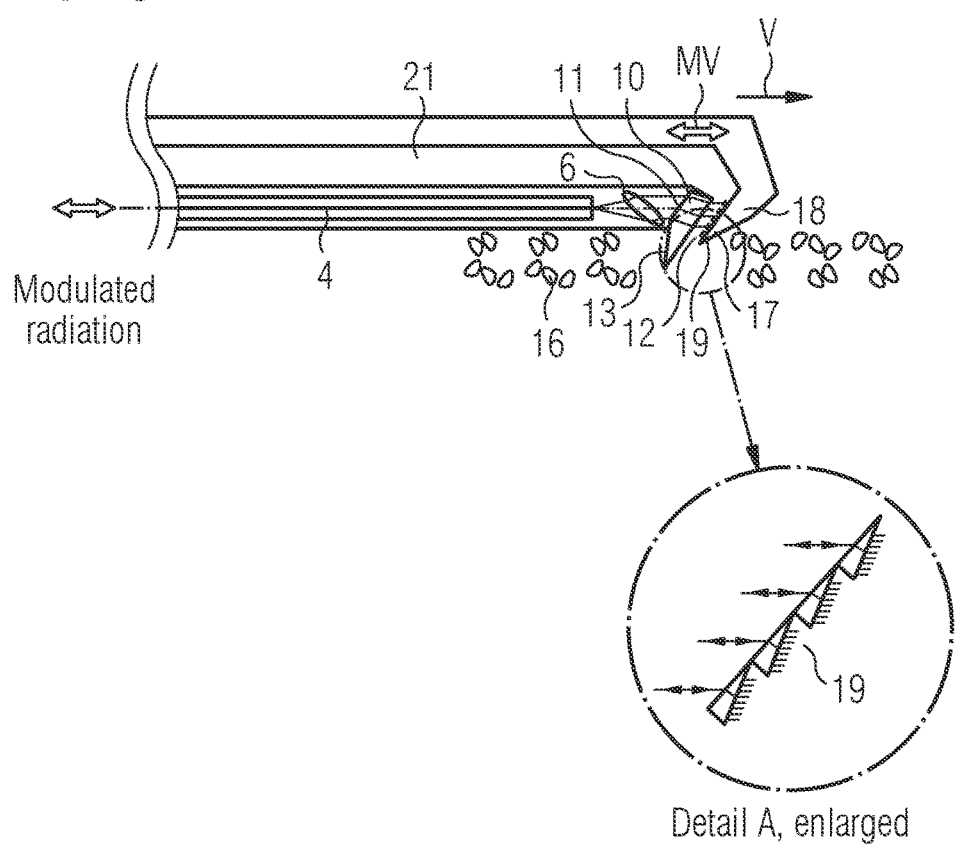
Detail A, enlarged

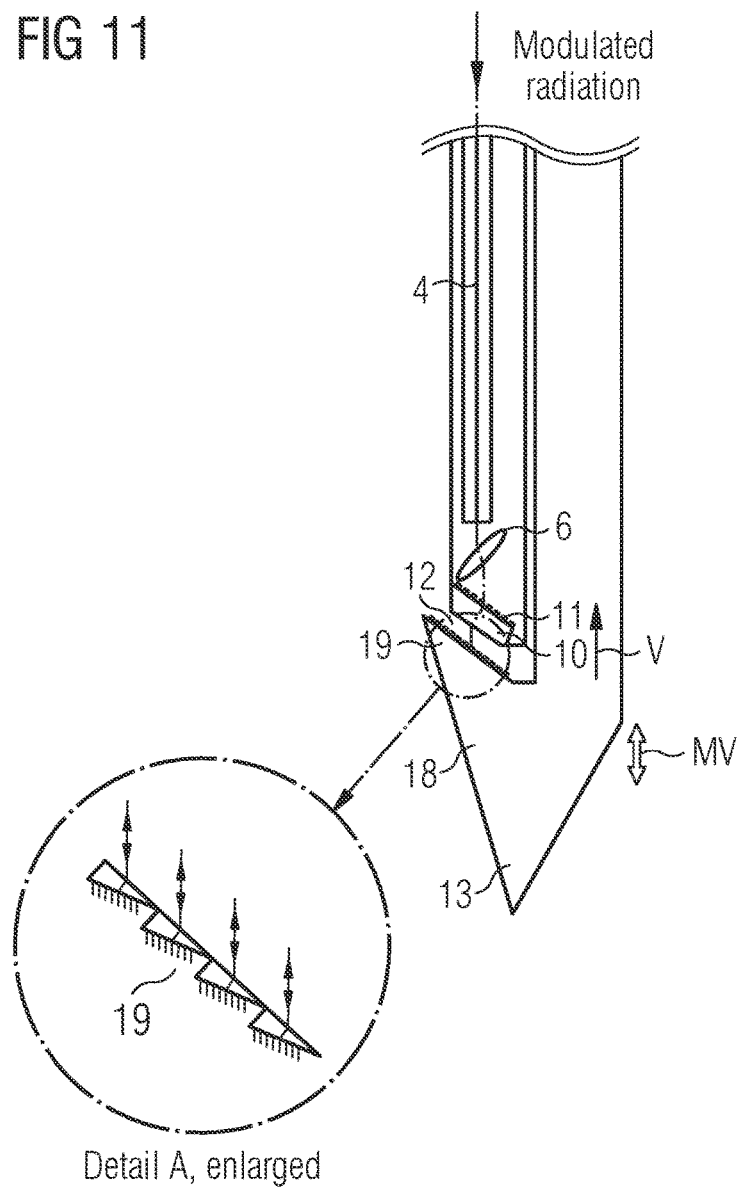

Cross-section A-A'

Tissue to be discarded after measuring absorption

Detail A, enlarged

Detail A, enlarged

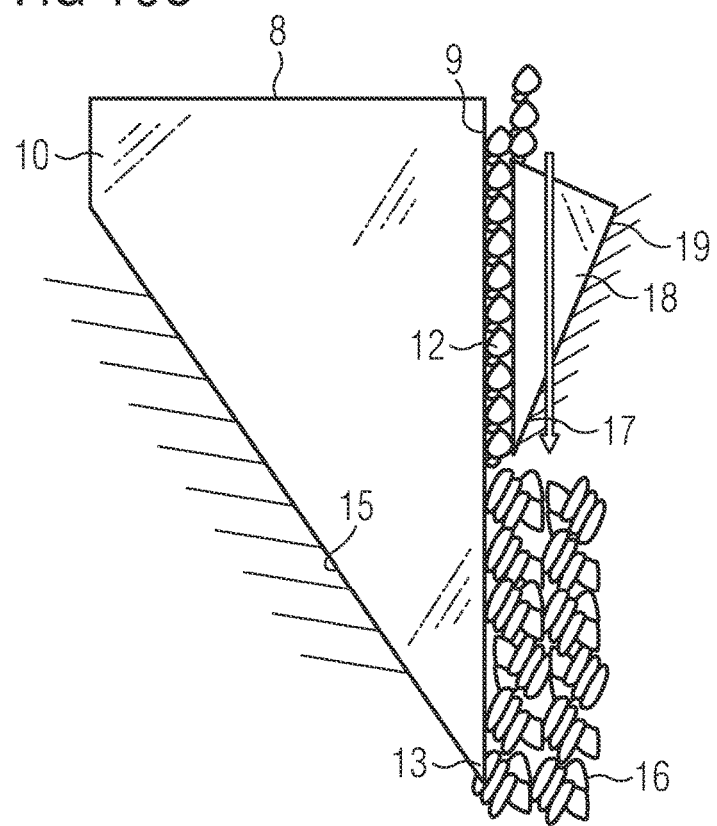

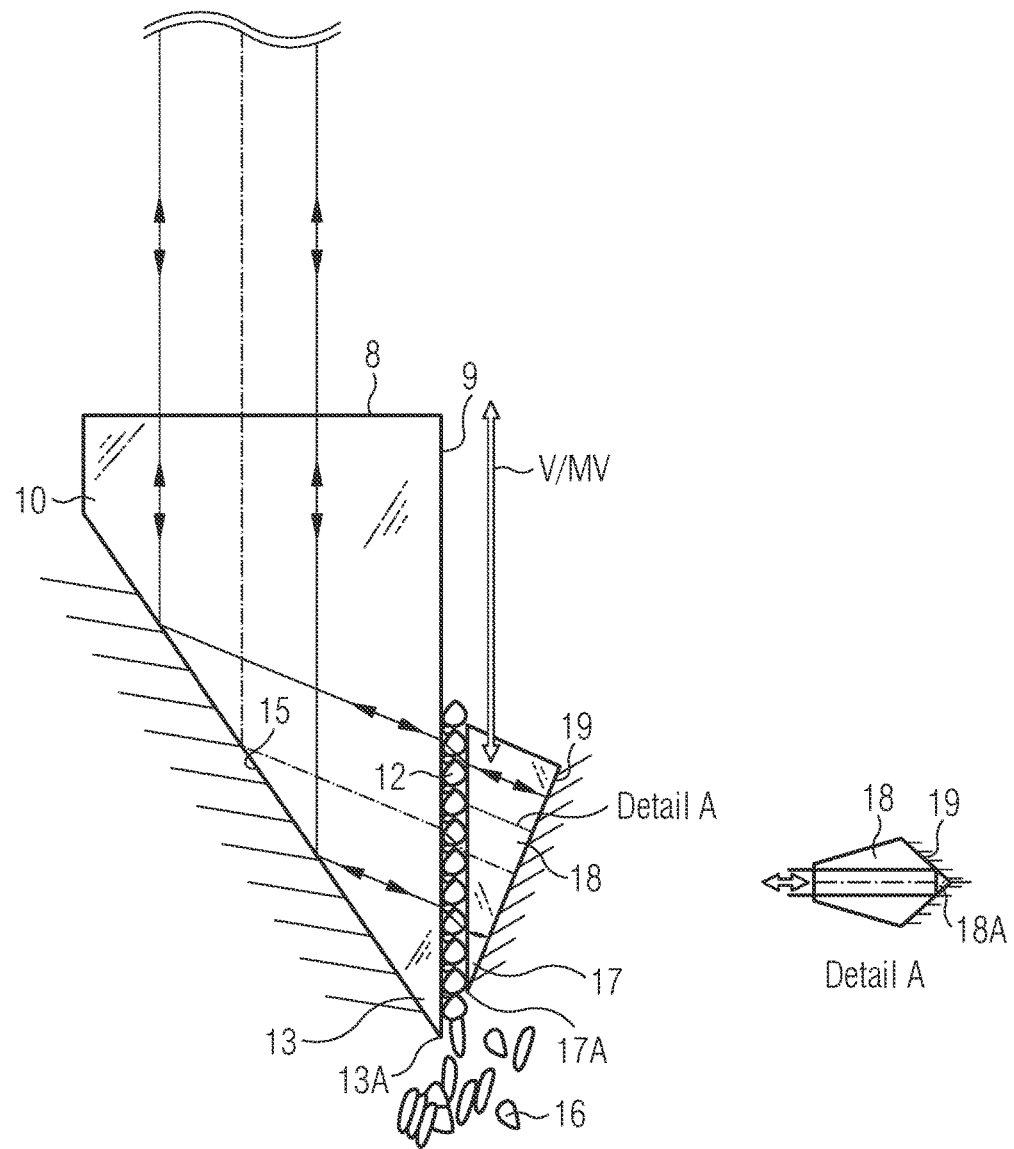

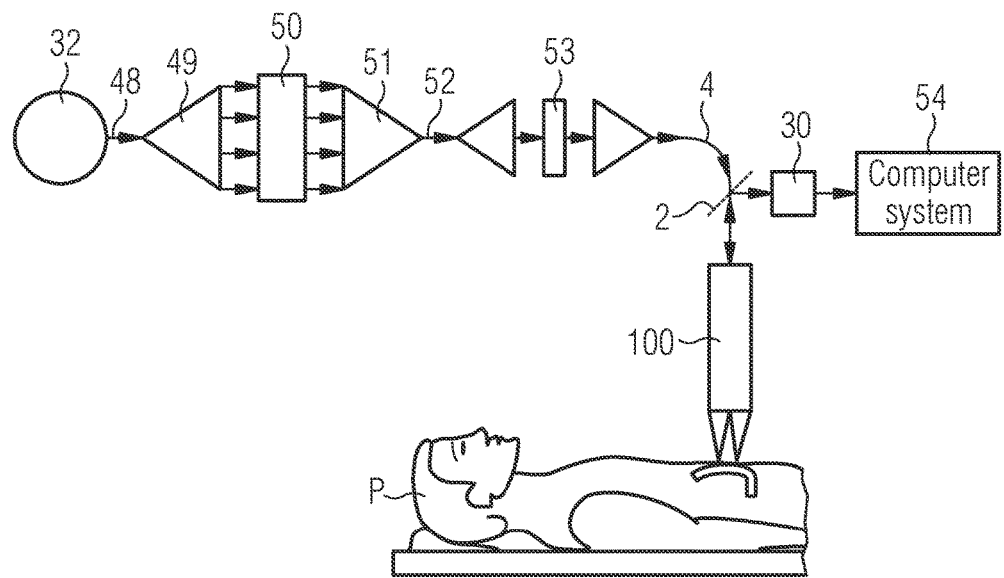
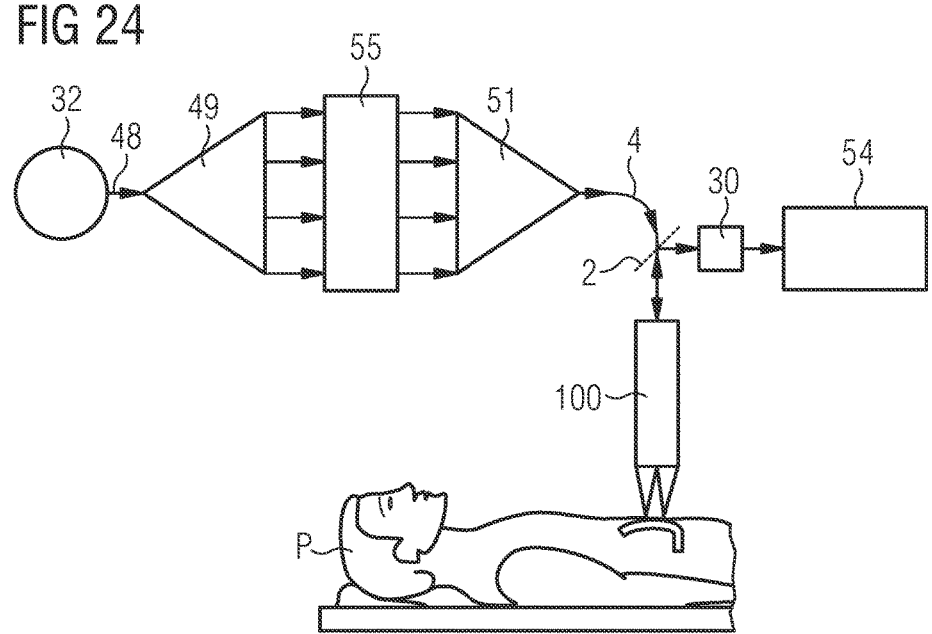

METHOD AND APPARATUS FOR OPTICAL ABSORPTION MEASUREMENTS

RELATED APPLICATIONS

The present application is a U.S. non-provisional filing of European Patent Application No. 14 003 225.1, filed on Sep. 17, 2014, and the present application claims priority to and the benefit of the above-identified application, which is incorporated by reference herein in its entirety.

BACKGROUND

The present invention relates to a measuring probe and an arrangement/a system for measuring spectral absorption, preferably using infrared radiation. Furthermore, the present invention relates to a method for spectroscopically measuring absorption.

A standard method for identifying cancer tissue is histopathological microscopic investigation by means of microscopy by an experienced histopathologist. Tissue samples are taken, cut and strongly diluted, dried if applicable and, if applicable, prepared chemically for spectral measurement by transmission or transflection. The tissue is analysed in the laboratory, frequently quite distant from where it was taken. Measurements therefore require a great deal of time and effort and strongly depend on the experience of the histopathologist. In addition, the known solutions are too voluminous for in-vivo applications and would significantly damage or destroy healthy tissue. This would lead to substantial collateral damage.

Likewise, methods are known for identifying cancer tissue that are based on infrared spectroscopy within the medium infrared range (MIR), in particular Fourier spectroscopy. Examples of such methods and devices for in-vivo measurement using infrared spectroscopy based on miniaturised attenuated total reflection (ATR) prisms in conjunction with Fourier transformation spectroscopy in the MIR range are known from U.S. Pat. No. 8,452,356 B2, for example.

However, given the methodology of ATR measurement, the ATR prisms used in the prior art are rather blunt and can easily damage or destroy the investigated tissue. ATR measurement is also strongly influenced by the pressure of the tissue on the totally reflecting surface of the ATR prism. The pressure cannot be easily influenced or ensured in-vivo, however, and is also not easily determined. However, the reliability of the measuring results strongly depends on the pressure. Furthermore, the spatial resolution of measurements based on ATR prisms is generally not very high.

BRIEF DESCRIPTION OF THE DRAWINGS

These and other objects, features, aspects, and advantage of the present disclosure will become better understood with regard to the following description, claims, and drawings. The present disclosure is illustrated by way of example, and not limited by, the accompanying figures in which like numerals indicate similar elements. Moreover, a list of reference numerals and corresponding explanations are provided in Table I.

FIGS. 3 to 19 illustrate exemplary measuring probes and arrangements for measuring absorption comprising the measuring probes in accordance with one or more aspects of the present disclosure.

FIGS. 23 to 25 illustrate exemplary arrangements for measuring absorption in accordance with one or more aspects of the present disclosure.

In the figures, the same reference numbers are used for the same or similar elements. For the sake of comprehension, the figures are not true to scale. In particular, the diffractive structures are highly enlarged and may not be depicted true to scale.

DETAILED DESCRIPTION

Figure 1:
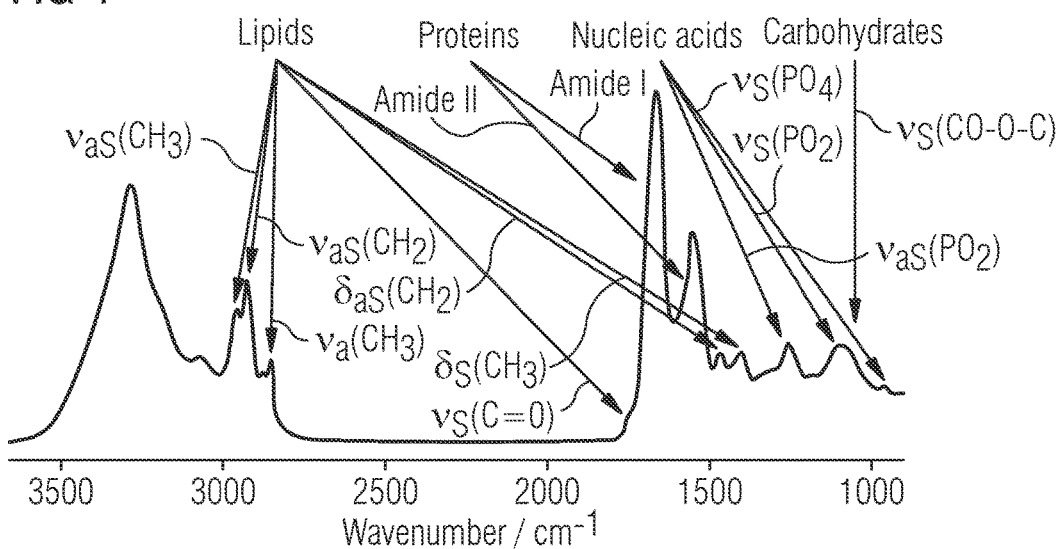
FIG. 1 illustrates an exemplary spectrum of typical biomolecules in accordance with one or more aspects of the present disclosure.

An objective of the invention is to provide an optical measuring device that can be built in miniaturized form (in particular in terms of its lateral extension) and/or that provides precise measurements in a preferably shorter time. In particular, an objective of the invention is to provide an optical measuring device for minimally invasive, in-vivo investigations of biological samples (e.g., tissue). An additional objective is to provide a corresponding optical measuring method.

To achieve the(se) objective(s), a measuring probe is provided for measuring spectral absorption according to a first aspect of the invention. The measuring probe comprises:
- a cutting apparatus which is designed to cut a slice or respectively flap off of a sample to be measured;
- a measuring gap which is designed to accommodate the sample slice; and
- an optical window element (in-coupling and out-coupling element) for coupling measuring light into and out of the measuring gap; and
- an end reflector which is designed and arranged to reflect the measuring light propagated through the measuring gap back into the measuring gap.

The measuring probe can be integrated in an arrangement/a system for measuring spectral absorption. The arrangement for measuring spectral absorption can furthermore comprise a light source and an apparatus for the spectral analysis of the measuring light coupled out of the measuring gap.

The measuring probe or respectively arrangement for measuring spectral absorption can for example be a measuring probe or arrangement for spectral measurements (e.g., molecular spectroscopy) in the visible range, infrared range (e.g., the NIR, MIR or FIR range), and terahertz spectral range, etc. Preferably, the measuring probe or arrangement for measuring spectral absorption is designed to perform measurements in the infrared range (IR), in particular in the middle infrared range (e.g., in the wavelength range from 6 μm to 11 μm, preferably from 7 μm to 10.5 μm). Within this range, some of the spectral key signatures for cancer tissue or respectively cancer cells serving as cancer markers can be located in the spectrum. For example, the relationship of the absorptions in the bands of 1080 $cm^{-1}$ and 1236 $cm^{-1}$ is an indication of the change in the numerical ratio of RNA to DNA which increases in the presence of cancer cells. Likewise, other cancer markers in the MIR range are known in the professional literature.

However, it is possible to use the measuring probe for measurements in the NIR range (e.g., for RAMAN spectroscopy) for fluorescence spectroscopy, etc. The light source can be a spectral broad-band light source, a multiwavelength light source with at least two wavelengths or respectively wavelength ranges, a source with tunable wavelengths, or a light source with an addressable spectrum.

The spectral broadband light source can e.g. comprise an (IR) broadband laser, a synchrotron light source (in particular in the IR range), or another suitable broadband light source. At a suitable dose, synchrotron radiation in the MIR does not generate any radiation damage (like energy-rich radiation, x-rays, etc.) in humans, but "only" thermal damage which is locally restricted (e.g., within a region of 0.01 mm to 0.1 mm). Due to the always present tissue water—including in the bone—there is an extremely strong (absorption) barrier in the body which prevents further damage to healthy tissue.

The multiwavelength light source can for example be or comprise a quantum cascade laser or a laser battery. Preferably, the quantum cascade laser is designed with a tunable wavelength.

The light source with the addressable or respectively addressed spectrum can for example comprise a modulation device which preferably has a plurality (i.e., at least two) modulation channels, each of which has a predetermined, different modulation frequency in the modulation channels within a predetermined modulation frequency range (e.g., 0.1 Hz to 10 MHz), whereas electromagnetic radiation of a different physical wavelength is assigned to each modulation channel. Furthermore, the light source with the addressable or respectively addressed spectrum can comprise a spectral broadband source, a device for spectral separation, and possibly a device for combining the individual modulated spectral channels. A light source with an addressable or respectively addressed spectrum is described for example in German patent application DE 10 2014 002 514.4.

The light source can be provided with at least one fibre output. Furthermore, the measuring probe or respectively the arrangement for measuring spectral absorption can comprise an optical channel (illumination channel) for transporting the measuring light emitted by the light source to the window element. The illumination channel can for example comprise a fibre, or consist of a fibre. The fibre can for example be a silver halide fibre. It is, however, possible to couple the measuring light emitted by the light source directly into the window element.

The illumination channel can comprise additional optical elements such as lenses, mirrors, etc. Preferably, the illumination channel comprises a collimator or a lens system for generating a substantially collimated, or respectively parallel, or slightly focused measuring light ray. It is furthermore possible to use a converging or respectively focused measuring light ray.

The measuring probe or respectively the arrangement for measuring spectral light absorption can furthermore comprise a spectral filter which is designed to filter out predetermined spectral bands, or respectively spectral ranges, from a broadband spectrum, or from a spectrum with several wavelengths or wavelength ranges.

Conventional broadband light sources can supply broadband light with a continuous or discrete spectrum which extends over several wavelengths or wavelength ranges. Frequently, however, the sought spectral signature is only found in a small number (e.g., 20) of absorption bands and/or their relationship with each other. The relevant absorption bands can be known beforehand and, for example, saved in a database. According to one aspect of the invention, when there is a limited number of previously known absorption bands that are relevant in a specific context (e.g., investigating cancer), it is proposed that only these relevant absorption bands be supplied, preferably with a specific spectral spread, for measuring the absorption of the sample, and then evaluated. This can reduce the radiation load introduced while measuring absorption. In this case, the measuring probe, or respectively the arrangement for measuring spectral absorption, comprises a filter which is downstream from the light source and is designed to filter out predetermined spectral bands from the broadband spectrum. The filter can for example be a frequency comb filter which is designed to basically only let pass through the spectral components relevant to measuring absorption where the relevant absorption bands are located with a certain probability. The frequency comb filter can for example be designed as a dispersive spectrometer with a diffraction grating. Within the region of spectral separation of the frequency comb filter designed as a dispersive spectrometer, highly reflecting and highly absorbing regions can be found, wherein the undesirable spectral components can be darkened by the strongly absorbing regions. The strongly reflected (desired, or respectively relevant) spectral components can be recombined in a focal point by means of diffraction in a diffraction grating and, for example, very efficiently coupled into a fibre (e.g., a monomode fibre).

Furthermore, the measuring probe or the arrangement for measuring spectral absorption can comprise an apparatus for the spectral analysis of the measuring light coupled out of the measuring gap. The apparatus for spectral analysis can for example be designed as a dispersive spectrometer, or as a Fourier transform spectrometer. Given a tunable source of electromagnetic radiation, it is possible for the apparatus for spectral analysis to only comprise the detector of electromagnetic radiation. Given a multi-spectral light source with an addressable spectrum, the apparatus for spectral analysis can comprise a detector of electromagnetic radiation and a device for analysing frequency over time (such as a Fourier or wavelet analysis) of the detected signal. In this case, the detector is preferably a rastered detector. The detector can for example be a detector (in particular an integral detector) for IR radiation, such as a mercury/cadmium/telluride detector (MCM detector) which is cooled with liquid nitrogen.

Furthermore, the apparatus for spectral analysis can comprise a time-scanning or 3-D dual beam interferometer downstream from a broadband or multi-wavelength light source.

The signal detected by the detector can be analysed by means of a signal evaluation device in order to obtain spectral features of the investigated (examined) sample and possibly assign these features to certain groups (e.g., healthy, ill, etc.). The signal evaluation device can at least comprise a computer or processing system which is programmed for example to perform a main axis transformation (PCA—principal component analysis) in order to perform a spatial and/or temporal Fourier analysis (in particular an FFT analysis), a wavelet analysis, a lock-in detection or another suitable analysis of the detected intensity profile, or respectively the detected temporal variation of the intensity.

Furthermore, the arrangement for measuring spectral absorption can comprise an optical channel (detection channel) for transporting the measuring light coupled out of the measuring gap to the apparatus for spectral analysis. The detection channel can comprise a fibre or consist of a fibre.

Furthermore, the optical channel can comprise other optical elements such as lenses, mirrors, etc. The detection channel can for example comprise focusing optics arranged before the detector. Preferably, a (fine) diaphragm (vignetting diaphragm) is arranged within the focal plane of the focusing optics to reduce undesirable scattered light (e.g., Mie scattering) and/or hide or at least reduce undesirable reflection spots which may be strong in certain circumstances. This holds true in particular when a laser is used (such as a QCL). The diaphragm can be designed as a slit diaphragm. The device for measuring spectral absorption can also comprise a plurality of detection channels which for example transport the measuring light in different spectral ranges to corresponding detectors. Accordingly for example, strong spectral splitting in the measuring probe (such as from the use of diffractive elements) can be taken into account.

In one preferred embodiment, the illumination channel and detection channel can share common optical elements. Thus, the illumination channel and detection channel can at least share a common fibre and/or a beam splitter. The measuring light can be coupled into the window element and coupled out of the window element via this common fibre. An advantage of this arrangement is that the measuring probe can be miniaturized, in particular in a lateral direction. In medical applications, the measuring probe can accordingly be designed to be more patient-friendly.

Preferably, the measuring probe is inserted in the sample (such as tissue) supported by vibration. The measuring probe can also be introduced into the sample guided by a robot arm.

The measuring probe furthermore comprises a cutting apparatus which is designed to cut a slice or flap off of a sample to be measured. In one example, a "quasi" infinite sample section is created which is transported past the measuring gap in the probe soon after being cut off. The cutting apparatus can be designed to create the sample slice by mechanical dissection (e.g., micro-planing, optionally supported by ultrasound and/or a vacuum). The cutting apparatus can also be designed to create the sample slice by means of a femtosecond laser microtome.

Since the cutting apparatus can be designed with a very sharp cutting tip or respectively cutting blade, the investigated sample (such as the investigated tissue) is only slightly damaged. Furthermore, it is possible to measure closer to the tip (in comparison to the prior art) so that even deeper regions of the sample can be measured. If in contrast a fine tip were used on an ATR prism known from the prior art to facilitate cutting, it would be impossible to also measure places within the depth of the tissue (such as the periosteum) since the ATR prism cannot reach these places.

Preferably, the cutting apparatus is designed to cut a sample slice or respectively flap with a thickness less than 100 µm, and preferably between 1 µm and 30 µm. Typically the thickness of the dissected sample slice or respectively flap is between approximately 4 µm to 12 µm. The slice (sample slice) cut out by the cutting apparatus is hence relatively thin and possesses two comparatively extensive boundary surfaces in relation to its small thickness which, for example are created by mechanical dissection.

One of the boundary surfaces of the sample slice can lie against a first window surface of the window element which is optically transparent to the measuring light. The first window surface accordingly constitutes one of the boundary surfaces of the measuring gap. The light is coupled into the measuring gap through the first window surface and, after passing twice through the sample slice in the measuring gap, is coupled out of the measuring gap. The other boundary surface of the sample slice can lie against a second window surface (i.e., a surface which is substantially transparent to the measuring light) of a second element (e.g., an end mirror support element), or directly against the end reflector. The second window surface or the end reflector in this case constitutes the second boundary surface of the measuring gap. At least part of the least partially cut off sample slice or separated sample slice pieces lie against each of the window surfaces, or against the window surface and end reflector, during the measuring process.

At least one of the two optical window surfaces (preferably both window surfaces) and/or the end reflector are preferably flat surfaces or slightly curved surfaces (e.g., surfaces with a radius of curvature greater than 500 µm), such as slightly curved spherical or cylindrical surfaces. The optical window element can furthermore have at least one flat or one curved surface with refractive power. The curved surface can be a spherical or an aspherical surface, such as a free-form surface. The curved surface can be the entry surface for the measuring ray into the window element, or another surface of the optical window element. The curved surface can for example be designed so that the incident measuring ray bundle is collimated.

The thin sample slice (e.g., a thin tissue flap) is transilluminated to, for example, measure the absorption spectra of molecules (e.g., biomolecules) for diagnostic purposes, or other measuring purposes, directly in the sample (e.g., directly in the tissue). In the process, the optical contact with the sample slice located in the measuring gap is created by an optical window surface of the window element.

The measuring light coupled into the measuring gap by the window element passes through the measuring gap to transilluminate the thin sample slice a first time in order to generate absorption there. The measuring light propagated through the measuring gap, or respectively the sample slice, then reaches the end reflector and is reflected back by the end reflector into the measuring gap. After the reflection at the end reflector, the thin sample slice is transilluminated a second time to again generate absorption in said sample slice. This produces an amplification of the measuring effect and makes it easier to realize a small measuring probe.

After the measuring light ray passes twice through the sample slice located in the measuring gap, the measuring light can either return into itself, at least approximately, to then be coupled into a detection channel, for example by beam splitting (auto-focus approach), or it propagates in a detection channel separate from the input bundle ray path (double focus approach). The photons of the measuring light which are not absorbed and not, or only slightly, scattered while passing twice through the sample, are detected by a detector.

Preferably, the cutting apparatus, the measuring gap, the optical window element and the end reflector and possibly other elements (e.g., the end reflector support element, removal channel, etc.) are integrated in a housing. The housing is preferably made of steel or another biocompatible material and has an elongated catheter, or respectively needle shape. Preferably, the measuring probe has a longitudinal shape with a longitudinal axis such as a probe, needle or catheter shape, wherein the diameter of the measuring probe preferably lies within the range of 0.8 mm to 3 mm, and the length of the measuring probe preferably lies within the range of 8 mm to 150 mm.

The cutting apparatus (which is preferably arranged in the tip of the measuring probe) preferably has at least one cutting blade which can have a plano-concave shape, wedge shape, plane shape, or another suitable shape. The at least one blade can for example be a hollow cutting-edge. The hollow cutting-edge can have a channel which terminate in the measuring gap. The cutting apparatus can also have a dual blade with a first and second blade. In this case, preferably each boundary surface of the thin sample slice, or respectively flap, is created by dissection with its own blade.

The at least one blade can be an integral component of the optical window element, or it can be connected (preferably securely or firmly) to the optical window element. The at least one blade can also be an integral component of the end reflector support element, or it can be connected (preferably securely or firmly) to the end reflector support element. Preferably, the connection between the at least one blade and the optical window element and/or end reflector support element is mechanically rigid and is realized along the shortest path. The connection can furthermore be an optical connection. By integrating the optical window element or the end reflector support element and the cutting apparatus into a single element which has both an optical function as well as a cutting function, the measuring probe can be constructed small and compact. Since the measuring probe has a small number of mechanical parts, the stability and robustness of the measuring probe can be increased.

The at least one blade preferably has a cutting tip or cutting edge with an angle (cutting angle) less than 90°, preferably less than or equal to 70°, more preferably less than or equal to 40°, particularly preferably less than or equal to 30°. Extremely thin sample slices (e.g., tissue slices) can hence be cut out of the sample without unnecessarily damaging (e.g., crushing) the sample.

In one example, the cutting apparatus can comprise a second cutting blade which is preferably designed to be movable relative to the first blade. The first and second blade form the front region of the measuring probe, or respectively the tip of the measuring probe.

The second blade can also have a plano-concave shape, wedge shape, plane shape or another suitable shape. The second blade can have two cutting surfaces which form a cutting tip or cutting edge with an angle less than 90°, preferably less than or equal to 70°, more preferably less than or equal to 40°, particularly preferably less than or equal to 30°.

In one example, the first blade can be an integral component of the optical window element or can be connected thereto (preferably securely or firmly). The second blade can be an integral component of an end reflector support element, or can be connected thereto (preferably securely or firmly). The reverse arrangement is also conceivable. In one example, the first blade and second blade can be designed and arranged such that the cutting surfaces of the first and second blade delimit or respectively shape the entry into the measuring gap, or respectively the sample entry. Expressed otherwise, the first and second blades arranged at a distance from each other can form a channel, or respectively sample entry area, which terminates in the measuring gap.

The first blade can for example be arranged such that one of the cutting surfaces seamlessly abuts a surface bordering the measuring gap such as the window surface of the window element, or the end reflector support element, or the end reflector. In one example, this cutting surface, together with the window surface or the end mirror, forms a wall bordering the measuring gap. One of the two cutting surfaces of the two blades can lie in the plane of the other surfaces bordering the measuring gap, and preferably seamlessly abut this surface.

Preferably, the second blade is arranged to be movable with respect to the first blade. The second blade can for example be movable along the longitudinal direction of the arrangement for measuring absorption, or respectively along the infeed direction, and/or along another direction (e.g., in a direction perpendicular or oblique relative to the infeed direction). In particular, the second blade can move relative to the main blade by an up and down oscillating movement which greatly facilitates the creation of a very thin tissue flap. The oscillating movement can have a small, high-frequency oscillating amplitude. Accordingly, the mechanical dissection process of the adjacent blade can be supported by vibration, or respectively micro-oscillations within the ultrasonic range. In addition to improving the dissection effect in the sample, the vibrations, or respectively micro-oscillations of the moving blade can cause the cut-off sample slice to be compressed. The measuring probe, or respectively the arrangement for measuring spectral absorption, can consequently comprise a control device for moving the second, and possibly the first blade (e.g., a piezoactuator, an electrically operated actuator, etc.). For a fine, highly-precise and low-friction adjustment of the movable blades, a micro-bearing can preferably be integrated in the measuring probe (e.g., an aerostatic micro-bearing) which bears the movable blade. In addition or alternatively, the micro-oscillations can act on the measuring probe as a whole. The energy required to move the blade and/or the measuring probe as a whole can for example be supplied by fluid (such as a gas or liquid) under pressure, electrically (such as by means of a piezo effect), heat (such as a bimetal), or in another form.

Preferably, the advancement of a movement by the movable blade can be a least one-half the length of the lateral scanning range during measurement. In the process, the length of the scanning range determines the spatial/local resolution of the measuring probe.

In one example, the cutting apparatus can comprise a primary blade and secondary blade for dissecting samples in order to create a comparatively thin sample slice (e.g., a comparatively thin tissue flap). Preferably, the primary blade of the measuring probe is arranged such that it always penetrates into deeper sections of the sample as the first blade while approaching the target area of the measurement. The secondary blade, which is preferably movable relative to the primary blade, remains behind the primary blade, i.e., it is never in front of the primary blade. In this case, the secondary blade can be designed smaller and weaker.

In one example, the primary blade can be an integral component of the optical window element or can be connected thereto (preferably securely or firmly). The optical window surface of the window element can be assigned to the primary blade. The secondary blade can be an integral component of an end reflector support element, or can be connected thereto (preferably securely or firmly). For example, either an optical window surface with a reflector (end reflector) behind the optical window surface, or only a front-end reflector, can be assigned to the secondary blade. The reverse arrangement is also conceivable.

More preferably, the at least one blade is made of a material transparent to the measuring light, and/or is securely or fixedly connected to components made of transparent material (preferably along the shortest path and in optical contact). For measuring light within the infrared range, the at least one blade can for example made of diamond. The advantages of this material are the high biocompatibility, the cutting ability, and the transparency within the MIR range in which important spectral information on the composition of organic samples can be obtained. Likewise, very thin and even sample sections can be created using diamond. A blade formed from diamond can hence simultaneously satisfy the functions of cutting, encapsulation and MIR transmission.

If the cutting apparatus comprises two blades, one or both of these blades can be made of a transparent material. At least one of the blades can however be made of a non-transparent material.

Preferably, both the first blade as well as the window element are made of diamond. The first blade and the optical window element can for example be components of a single element that has both a cutting function as well as an optical function. This element can for example be a prism (hereinafter designated a primary blade prism), such as a prism with flat or curved (e.g., spherical or aspherical) surfaces. The prism has the optical window surface bordering the measuring gap and a light entry surface which can be a flat or curved (e.g., a spherical or aspherical) surface. The light entry surface on the primary blade prism can be at a slight angle relative to the axis of the incident light bundle such that reflections on the same can be (largely) blocked by a diaphragm (vignetting diaphragm) in the detection ray path.

Furthermore, the cutting apparatus can at least comprise an auxiliary blade which cuts through the sample slice at the narrow edge. The cut-off sample slice can be removed from the arrangement, or at least temporarily stored in a reservoir in the arrangement.

The measuring gap can for example be parallel or wedge-shaped with an angle less than 1° and preferably less than 0.1°.

In an arrangement having a parallel measuring gap, an undesirable spectrum can arise that is caused by multiple reflections in the nearly parallel measuring gap and overlaps the measuring signal (a so-called channelled spectrum or standing wave problem).

The problem of the undesirable channelled spectrum can be reduced by absorption in the tissue flaps, which is not overly small due to the selected flap thickness and the double ray path. Furthermore, the effect of the undesirable spectrum can be reduced by an antireflective layer on the surfaces bordering the measuring gap. It is furthermore possible to calculate the overlapping undesirable spectrum out of the detected measuring data, for example by a numerical differentiation of the spectral data. Given the small gap, which means only a few wavelengths of optical path difference (OPD) for the effect of the undesirable channelled spectrum, the effect of the undesirable channelled spectrum causes rather long-period modulations over the wave number which can be numerically calculated out.

Furthermore, the measuring gap can be arranged such that the angle of incidence of the ray bundle at the surfaces bordering the measuring gap is different from 90°. In this case, the individual reflections can only cause an undesirable channelled spectrum to a limited extent. However in this case, an undesirable partial bundle pair generated by a zigzag reflection on the window surfaces can coherently overlap the measuring bundle since it possesses the same direction of propagation in the parallel gap.

The effect of the undesirable channelled spectrum can be further reduced by a wedge-shaped design of the measuring gap since even slightly tipping the undesirable partial bundle relative to the measuring bundle attenuates the effect of the undesirable channelled spectrum. The wedge angle can be selected so that the change in wedge thickness is approximately one-half the average wavelength along the effective measuring length in order to arrive at the first zero position of the interference modulation by means of the integration effect over the measuring surface. With an aqueous medium, a change in the wedge thickness of 3 µm to 4 µm along the measuring length is sufficient (gap height/gap length). One disadvantage of the arrangement having a wedge-shaped measuring gap is however that, due to the wedge-shaped measuring gap, or respectively the wedge-shaped sample slice, the absorption significantly depends on the location of the measuring gap, and the measuring field is therefore weighted.

The width of the measuring gap is preferably less than 200 µm, preferably less than 100 µm, more preferably equal to or less than 50 µm, and particularly preferably equal to or less than 20 µm. The width of the measuring gap is preferably variable.

In particular when measuring aqueous samples (e.g., tissue) within the infrared, it can be advantageous, due to the extremely strong water absorption, to keep the thickness of the sample slice to be measured low. Preferably, the thickness of the sample slice to be measured is approximately or less than $\lambda\_ave/2$ to $\lambda\_Ave$, wherein $\lambda\_ave$ is the average wavelength of the spectrum of the measuring light (for example less than or equal to 10 µm to 5 µm for an average wavelength of, for example, 10 µm). Since it can be difficult to cut off such a thin sample slice, it can be advantageous to additionally thin out and/or dehydrate the cut-out sample slice before measuring. The water content of the compressed, or respectively thinned-out sample slice is less, which generally leads to an improvement in the signal-to-noise ratio, a decrease in measuring time, and less required calibration.

Thinning out and/or dehydrating the cut-out sample slice can for example be achieved by designing the measuring gap so that its width is variable. Accordingly for example, the window element and the second element bordering the measuring gap (e.g., an end mirror support element) can be designed to be movable relative to each other. With a measuring gap which is arranged oblique to the vertical direction, or respectively to the longitudinal axis of the measuring probe, the width of the measuring gap can for example be varied by a vertical movement of one or both of the elements bordering the measuring gap. Preferably, the movable elements are mounted on a micro-bearing (e.g., on aerostatic micro-bearing).

For example in a first measuring position, the measuring gap can be opened wider so that the sample slice cut out by means of the cutting apparatus (e.g., a sample slice having a thickness of 20 µm to 30 µm) can be conveyed into the measuring gap. After the sample slice is introduced into the measuring gap, the width of the measuring gap can for example be reduced to 5 µm to 10 µm in a second measuring position. The aqueous sample slice located in the measuring gap is accordingly "squished," and its water content is reduced. The measurement of the absorption spectrum can be performed in this position. In another embodiment, the width of the measuring gap can be initially minimal (e.g., approximately zero). In this state, the measuring probe can be introduced into the depth of the sample to be measured (such as the tissue). Once the probe is in the sample (located at a useful position), the fine measuring gap can be opened in order to cut off a sample slice. The sample slice is then preferably compressed by reducing the width of the measuring gap.

A dehydration of freshly dissected tissue in the measuring probe can furthermore be achieved by:
 micro-vibration of the measuring probe by means of which the water is slightly "shaken out" of the dissected tissues;
 the use of pulsed lasers and moderately heating the tissue;

the use of a laser at a wavelength of 3 µm since water absorption is particularly high at that point;

the use of microwaves if the probe is designed metal-free;

the use of cold, dry purging gas (N2).

Combinations of several of the above methods are also possible.

The measuring probe, or respectively the arrangement for measuring spectral absorption can consequently comprise at least one controllable device for pressing and/or compressing the sample, and/or for reducing the water content. Furthermore, the measuring probe, or respectively the arrangement for measuring spectral absorption, can contain a controllable device for opening and closing the measuring gap, or respectively the measuring volume. This for example makes it possible for the probe to first penetrate deeply and open and close a miniature door in the front area of the probe only upon reaching the target area. The energy required to execute the above functions can for example be supplied by fluid (e.g., a gas or fluid) under pressure, electrically (such as by means of a piezo effect), heat (e.g., a bimetal), or in another form.

Given sufficiently thin sample slices and sufficiently strong measuring light, the sample does not have to be compressed and/or dehydrated.

The measuring probe can have an elongated shape with a longitudinal axis, and the measuring gap can be arranged at an angle to the longitudinal axis of the measuring probe which differs from zero, i.e., oblique to the longitudinal axis. The angle between the longitudinal direction of the measuring gap and the longitudinal axis of the arrangement can for example be from 3° to 70°, preferably from 10° to 60°, and more preferably from 20° to 50°.

In one example, the longitudinal axis of the measuring probe at least approximately corresponds to the infeed direction of the measuring probe (i.e., the longitudinal axis of the measuring probe is substantially parallel to the infeed direction).

The oblique arrangement of the measuring gap makes it possible to squeeze, or respectively compress the cut-off sample slice (e.g., the tissue slice) by means of a purely vertical movement in the probe and/or the second blade. For measurements within the medium infrared, the thickness of the measured sample slice can preferably be reduced to a thickness between 1 µm and 30 µm, typically between approximately 4 µm to 12 µm. In particularly with aqueous samples (e.g., tissue samples), a reduction of loss from water absorption within the MIR can accordingly be achieved. Furthermore, the effect of the undesirable channelled spectrum can be reduced by an oblique arrangement of the measuring gap. An additional advantage of an oblique arrangement of the measuring gap is that it can be easier to dispose of the measured sample slice to the side. This facilitates a more compact design of the arrangement for measuring absorption.

The measuring gap can however also be arranged substantially parallel to the longitudinal axis, i.e., the angle between the longitudinal direction of the measuring gap and the longitudinal axis of the measuring probe is preferably substantially 0°. The ability to miniaturize the probe can be an advantage of this arrangement. To avoid direct reflections at the boundary surfaces, a diffractive optical element can be used for the end reflector as will be described in detail in the following.

The measuring probe moreover comprises an end reflector which is arranged on a end reflector support element. The end reflector support element can be securely or firmly connected to one of the blades of the cutting apparatus as described above.

The end reflector can be arranged on one of the surfaces bordering the measuring gap, or in the proximity of a surface bordering the measuring gap (front-end mirror). In this example, the measuring gap is at least partially bordered by the window surface and the end reflector. The end reflector support element can, but does not have to be, transparent to the measuring light. Accordingly, the end reflector support element can be made of a suitable hard material such as metal, ceramic, diamond, etc.

The end reflector can, however, be arranged on another surface of a substantially transparent end reflector support element (so-called rear end reflectors, or end reflectors "in the background"). The rear end reflector, or respectively end reflector "in the background", is preferably at an angle relative to the flat surface of the window element. This prevents an undesirable recordable channelled spectrum, or at least weakens its effect which distorts the measuring results.

The end reflector can for example be a mirror, in particular a flat mirror, such as a mirror made of gold, etc. In this case, the end reflector is preferably realized as a rear mirror, or respectively rear end reflector. The end reflector, which is preferably designed as a rear end reflector can be designed as a rooftop mirror prism, for example made of diamond or ZnSe.

In another example, the end reflector which is for example designed as a front or rear end reflector, can comprise a diffractive optical element (DOE), or be such an element. The diffractive optical element can be a reflective diffraction grating (such as a micro-profiled, blazed reflective diffraction grating), or comprise a reflective diffraction grating. In this example, the end reflector can be designed both as a front as well as a rear mirror. The micro-profile can for example have the shape of stairs, saw teeth, a rooftop or prism, or another suitable shape. The end reflector can for example have a triple micro-cat's-eye structure or rooftop shape in the reflector surface. This makes it possible to minimize the volume of the measuring probe design. The depth-profiled microstructure can for example be formed in solid metal, or in a sufficiently thick metal layer on the end reflector support element.

With a diffractive end reflector as the front mirror, or respectively front reflector, the DOE is preferably designed as a buried DOE. The sample slices can slide between the smooth walls of the measuring gap so that measurements of extremely thin sample slices are also possible. Preferably there are no microedges of the DOE in the region of the window surfaces, or respectively of the optical window of the measuring gap. A micro-profile (grip) can be arranged outside of the optical window (e.g., on the blades and/or above the measuring channel) so that the sample slice can be more easily transported "upwards" into a discharge channel, for example by microvibration.

The end reflector can be substantially flat or slightly curved. The normal of the end reflector can be at least approximately parallel to the normal of the window surface, or the surface region in the centre of the window surface. The end reflector can, however, be at an angle relative to window surface such that the normal of the end reflector is not parallel to the window surface, or the surface region in the centre of the window surface. This has the advantage that an undesirable recordable spectrum (the so-called channelled spectrum) is avoided, or its effect which distorts the measuring results is attenuated.

In one example, the end reflector can be at least approximately cylindrically curved. Preferably, the axis of the cylindrical compensation surface of the end reflector at least approximately coincides with the longitudinal axis of measuring probe. Furthermore, the end reflector can be a micro-profiled DOE or comprise such an element which preferably has a cylindrical phase function (e.g., a micro-profile). An advantage of this arrangement is the one-dimensional focus which allows an elongated surface of the sample to be transilluminated.

The end reflector is preferably a retroreflector. It is accordingly possible to use the same optical channel for transporting the measurement radiation to the measuring gap, or respectively for illuminating the sample, as well as for detection. The measuring probe can accordingly be constructed with a few number of optical elements which makes it possible to miniaturize the probe.

The diffractive end reflector can be designed for the first order of diffraction. It is, however, possible to design the diffractive end reflector for another order of diffraction. Preferably, the diffractive optical element is designed to optimize the transportation of the ray for detection, or respectively in a detection channel.

The angle of incidence of the main ray of the incident bundle in a substantially non-scattering medium (e.g., water, tissue secretion, etc.) at the compensation surface of the diffractive reflector is greater than or equal to 15°, and the angle between the incident main ray of the incident bundle and main ray of the departing bundle at the aforementioned compensation surface is less than twice the angle of incidence of the main ray of the incident bundle at the reflector surface. This can for example be achieved by a suitable design of a diffractive optical reflector with a blazed microstructure.

The most complete re-entry feasible into a detection channel or into a common illumination and detection channel, is preferably ensured for the broad-spectrum electromagnetic radiation entering the measuring probe. Uncompensated chromatic transverse aberrations can hinder or even prevent this. A first option is to use a fibre with a sufficiently large fibre core to transport the measuring light. This has the disadvantage that the arrangement for measuring absorption is enlarged.

Another option is to sufficiently limit the chromatism of the arrangement so that no major loss arises from chromatic transverse aberrations. Preferably, the optical arrangement is at least partially achromatic, or respectively achromatised. To achieve this, the measuring probe can for example comprise at least one compensation diffraction grating which is designed to at least approximately achromatise the optical system of the measuring probe, preferably up to detection. This can improve the efficiency of the measurement radiation. Furthermore, suppression of interfering light (reflection) in the detection channel can be achieved since the compensation grating can be designed so that the smallest possible amount of undesirable interfering light is coupled into the detection channel.

The compensation diffraction grating can in particular be designed to least partially compensate for the chromatic aberrations arising from the use of a diffraction grating as the end reflector. In addition or alternatively, the compensation diffraction grating can be designed to at least partially compensate for other chromatic flaws in the optical elements of the arrangement for measuring spectral absorption.

The compensation diffraction grating can for example be a reflective diffraction grating, a transmission diffraction grating, or another suitable diffractive optical element.

In one example, the compensating diffraction grating is arranged on the surface of the optical window element. The diffractive optical element can for example be arranged on the light entry surface of the optical window element. The diffractive optical element can be arranged on an additional optical element such as on a prism, a lens, etc. If in particular optical elements made of diamond are used, it can be advantageous to form the compensation diffraction grating on an additional optical element made of ZnSe since diamond is difficult to micro-profile. The additional optical element made of ZnSe can, but does not have to be, securely/firmly connected to the optical element made of diamond.

Preferably, the optical system of the measuring probe, or respectively the arrangement for measuring spectral absorption, is designed such that the incidence of the measuring light at the refractive optical surfaces of the arrangement is not perpendicular. Expressed otherwise, the optical component of the measuring probe, or respectively the arrangement, can be designed and arranged such that the angle of incidence of the light at the refractive surfaces of the measuring probe, or respectively the arrangement, is different than 0°. Preferably, the angle of incidence at the refractive surfaces is relatively small, and is only large enough to prevent direct reflection into the detection channel. Preferably, the angle of incidence is 10°, and particularly preferably 5°.

If the angle of incidence is 0°, undesirable reflections such as that described above can be minimized by using diffractive optical elements. Alternatively or in addition, the refractive surfaces can be AR-coated.

Another option for avoiding undesirable reflections in the detection channel is to use a plurality of detection channels. Accordingly, three detection channels such as three detection fibres can be used for a light source with three MIR lasers with different wave numbers or respectively wavelengths (e.g., 1084 cm$^{-1}$, 1235 cm$^{-1}$ and 1650 cm$^{-1}$). This is, however, rather large to construct and is therefore not patient-friendly. It is likewise possible to use the diffractive elements in the measuring probe due to the required ray deflection and employ the resulting spectral separation in combination with different detection channels.

Furthermore, the window element and end mirror are preferably designed and arranged such that the main ray of the measuring ray bundle exiting the window surface of the window element is angled at least approximately toward the centre of the window surface, wherein the angle of inclination is preferably greater than the marginal ray angle of the measuring ray bundle. With this arrangement, it is possible for basically no or little light to be reflected back into the illumination and/or detection channel (for example into the fibre core of an illumination and/or detection fibre). This minimizes the distortion of the measuring signal from undesirable interfering light.

Furthermore, the measuring ray bundle is preferably substantially parallel, or respectively collimated. The measuring ray bundle can for example be parallelised by at least one optical element of the measuring probe. It is, however, possible to also use focused ray bundles.

The measuring probe can furthermore comprise a removal channel for discharging from the measuring gap the sample slice located in the measuring gap. Likewise, the measuring probe can comprise a reservoir for accommodating and/or intermediately storing the sample slice discharged from the measuring gap. One advantage of the measuring probe with the end reflector according to the invention is that it is unnecessary to arrange the removal channel between two fibres, which would make it very difficult to miniaturize the sample.

The cut-off and measured sample slice can be discharged from the measuring gap. This can for example be accomplished by vibration by means of a suitable vacuum device, etc. The discharged sample slice can be permanently or temporarily (such as just for the time of measuring) stored in a reservoir (preferably in a micro-reservoir). The stored sample slice(s), or respectively sample cut(s), can be suctioned off in situ or extracted or removed by other means. If needed, the sample cuts can be supplied for an additional histopathological investigation. The data obtained from this investigation can be compared, or respectively contrasted, with the spectral data of the in situ probe measurement. The results can be documented in a record (e.g., in a surgical record).

In one example, the 3-D position of the measuring probe can be detected and for example tracked in real time. For this purpose, the arrangement for measuring spectral absorption can comprise a device for detecting the 3-D position of the measuring probe. The device for detecting the 3-D position can be an ultrasound imaging device, a CT (computed tomography) device, or another suitable device. The 3-D position of the measuring probe can be fed to a central processing system.

According to an additional aspect of the invention, a method for measuring the spectral absorption of the sample by means of the measuring probe, or the arrangement for measuring spectral absorption, is proposed according to one aspect of the invention. The method comprises the steps of:

accommodating or receiving a sample slice in the measuring gap of the measuring probe;
performing at least one spectral measurement of the sample slice located in the measuring gap, comprising:
coupling-in measuring light into the measuring gap through the window element, and transilluminating the sample slice located in the measuring gap;
reflecting the measuring light once propagated through the sample slice at the end reflector back into the measuring gap, and again transilluminating the sample slice located in the measuring gap;
coupling-out the measuring light, which was propagated twice through the sample slice located in the measuring gap, out of the measuring gap through the window element;
detecting at least part of the coupled-out measuring light.

Preferably, the spectral measurement is repeated several times, wherein each new measurement is carried out at a new spatial position in the sample, for example at a new depth and/or at a new lateral position. Preferably, while measuring the detected spectrum is assigned to the respective depth position and/or lateral position of the measuring probe in the sample to be investigated, thereby yielding the spectral distribution with spatial/local resolution. Preferably, the depth position and/or the lateral position of the measuring probe in the sample is measured continuously or repeatedly at brief intervals and for example saved in a memory. The measuring probe can execute a back-and-forth helical movement and thereby thinly dissect the tissue samples and supply them for the spectroscopic investigation.

In particular, the absorption can be measured as the measuring probe penetrates to an increasingly deeper region of the probe tip such that a scan of the depth (with the respective absorption spectrum) can be obtained locally at freely selectable measuring intervals and at a freely selectable measuring point density. It is likewise possible to perform a lateral scan. In one example, a multi-point recording (e.g., 5×5 pixels with a 100 μm diameter) can be taken in a lateral scan (for example by a lateral microscan of a monomode fibre at the inlet to the measuring probe). An average can be determined from the individual recordings. This reduces the probability of running into a "hole" in the sample (e.g., a "tissue hole"). In this case, a measuring probe with a numeric aperture Na of 0.05 to 0.1 is preferably used.

The method for measuring spectral absorption can furthermore comprise a two or three-dimensional measurement of the shape of the sample to be measured. Accordingly, the measuring volume, its location in the sample to be investigated (e.g., an organ, system or component) and the spectral distributions of the respective absorption measurements can be assigned to each other with minimal errors. The status of the measured sample can be evaluated by computer or using human expertise. During surgical operation, optimum incision lines can, for example, accordingly be identified.

The method can furthermore comprise a spectral analysis of the detected measuring light, and can optionally comprise a classification of the investigated sample slice into one of several categories.

Likewise, the method for measuring spectral absorption can comprise cutting off from the sample a sample slice of an at least approximately constant thickness, for example by means of the above-described cutting apparatus. The cutting is preferably carried out by mechanical dissection using at least one sharp blade.

As described above, the at least one blade can execute an up and down oscillating movement. This can strongly favour the creation of a very thin sample slice. The oscillating movement can have a small oscillating amplitude with a high frequency, such as a 0.5 μm oscillating amplitude and a 2 kHz frequency. In one example, at least one blade can oscillate, or respectively vibrate, within the ultrasonic range.

In one example, each of the boundary surfaces of the sample slice is mechanically cut off by an independent blade. As described above, one of the two blades can be the primary blade, and the other blade can be the secondary blade. In this case, the cutting off of a sample slice can comprise introducing the primary blade into the sample followed by introducing the secondary blade. In the process, the secondary blade can execute an oscillating movement relative to the primary blade.

In one example, the advancement of a movement by at least one movable blade can be a least one-half the length of the lateral scanning range. In the process, the length of the scanning range determines the spatial/local resolution of the measuring probe.

After being coupled out of the measuring gap, the measuring light can at least approximately return back into itself (retroreflection), or respectively be guided back into itself, in order to be subsequently coupled into a detection channel. The measuring light can, however, be coupled into a detection channel separate from the input bundle ray path.

The method for measuring absorption can furthermore comprise a change in the width of the measuring gap of the measuring probe. In particular, the method can comprise opening and closing the measuring gap (which, for example, is designed in the shape of a micro-gripper at the probe tip), possibly only at a previously-defined target location. Unnecessary damage to the investigated sample can accordingly be prevented. Furthermore, a change in the width of the measuring gap can lead to a compression or dehydration of the sample slice accommodated in the measuring gap.

The method for measuring spectral absorption can accordingly comprise a compression or dehydration of the sample slice accommodated in the measuring gap. As described above, the compression or dehydration of the sample slice accommodated in the measuring gap occurs before the actual measurement. The step of compressing or dehydrating the sample slice can however be omitted, for example if sufficiently thin sample slices and/or sufficiently strong light sources are used. Also when the measuring probe is used in the NIR range for RAMAN spectroscopy, the step of compressing or dehydrating the sample slice can be omitted since the above-described water barrier does not exist in RAMAN spectroscopy.

One advantage of the measuring probe according to one aspect of the invention is the possibility of miniaturizing the measuring probe, in particular its lateral extension (transverse extension, thickness, diameter). In medical applications, the measuring probe can accordingly be designed to be more patient-friendly. It is furthermore possible to perform a much more spatially filner survey of the sample (e.g., of a living organ). On the one hand, this makes it possible to largely retain the functionality of the sample and, on the other hand, supplies reliable and traceable data on the state and/or nature of the sample. With the measuring probe according to the invention, it is furthermore possible to measure more closely to the tip of the measuring probe (in comparison to the prior art) and accordingly also measure locations within the depth of the tissue without unnecessarily damaging the tissue.

Further advantages can be the short measuring time and/or the high informative value of the measuring data, or respectively the low measuring uncertainty in the absorption bands, since pressure in particular does not have any influence on the measuring results, and measuring artefacts (e.g., from light scatter or standing waves) can be minimized in the optical primary signals. Likewise, improved lateral resolution can be achieved.

Furthermore, it is unnecessary to fix the investigated sample (e.g., the investigated tissue) (e.g., by paraffining or freezing). The sample can be measured in its largely original state (e.g., in the original hydrated or slightly dehydrated state) directly (i.e., within a few seconds or minutes) after cutting, which increases the informative value.

The measuring probe, the arrangement and/or the method for measuring spectral absorption can be used in vivo in surgeries for soft tissue or to analyse soft parts or technical soft materials. It is also possible to measure hard tissue (e.g., cartilage) in vivo, which is very difficult or even impossible in the prior art given the high pressure.

The measuring probe, the arrangement and/or the method for measuring spectral absorption can be used in various medical and veterinary applications.

Accordingly, the measuring probe, the arrangement and/or the method for measuring spectral absorption can be used for a minimally invasive determination of the absorption spectra of soft tissue or cartilage (e.g., during surgical operation, preferably in real-time or quasi-real-time), in particular for determining molecular absorption spectra in the medium infrared spectral range since, according to present knowledge, the greatest significance and informative value of the spectra (molecular vibrations) exist at that range.

With reference to the determined absorption spectra, a quick and reliable assessment can be made (for example during surgical operation) about the presence of a tumour and/or the phase of the tumour's development (e.g., premalignant, malignant, benign, or intermediate stages). Furthermore, incision lines along which the tissue is to be cut out can be determined, preferably automatically, with a great deal of accuracy and precision, and provided to the surgeon.

Outside of surgical operation, the measuring probe, the arrangement and/or the method for measuring spectral absorption can be used for in vivo measurements of soft tissue, cartilage and/or bodily fluids (e.g., secretions, urine, etc.) in preventative medicine and/or in cases of suspicion. For example, a tissue analysis including a metabolic analysis can be performed using the spectral data.

The measuring probe, the arrangement and/or the method for measuring spectral absorption can also be used in various technical applications. It is accordingly possible, for example, to determine the absorption spectra of soft materials, preferably in real-time during operation, with minimal damage to the material. Technical applications comprise:

Veterinary medicine and animal breeding;
Material sciences;
Inspecting foods, for example inspecting imports and exports, or monitoring the production of foods;
Forensics and criminology;
The automated analysis of samples in biotechnology, medicine and chemical production.

Figure 2:
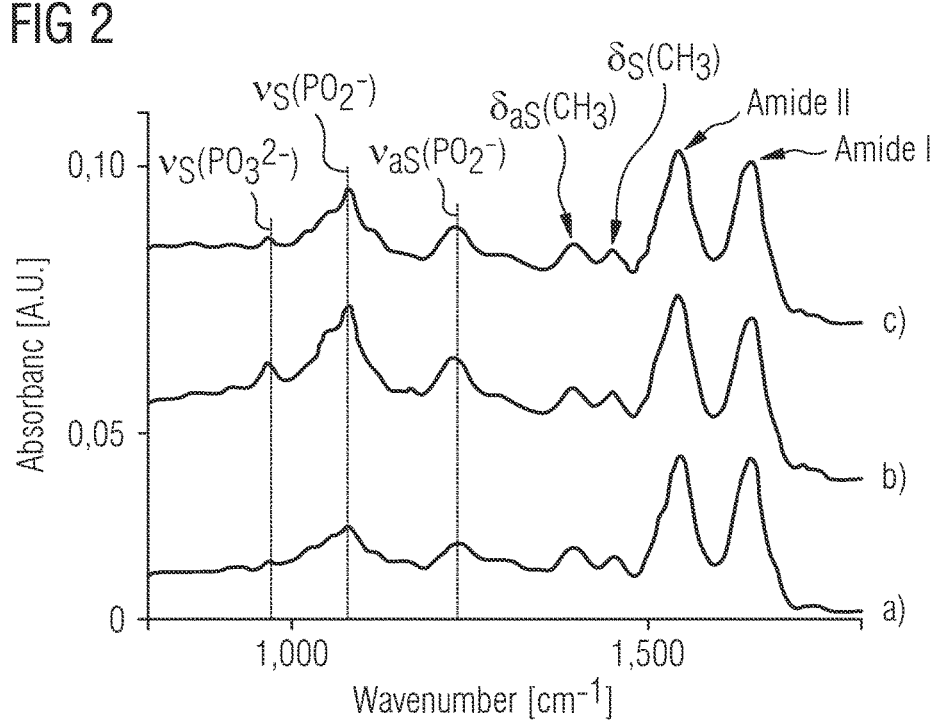
FIG. 2 illustrates exemplary absorption spectra of typical biomolecules in accordance with one or more aspects of the present disclosure.

Referring now to FIGS. 1 and 2, these figures show spectra (absorption spectra) of typical biomolecules. FIG. 1 shows spectra of typical biomolecules which are components of living cells (ref. Hughes, Caryn [Thesis], Development of Fourier Transform Infrared spectroscopy for Drug Response Analysis, Fig. 3.6, p. 83, University of Manchester, 2011). FIG. 2 shows the spectra of normal cells and cancer cells of the lung in the technical article "Infrared spectroscopy characterization of normal and lung cancer cells . . . " by So Yeong Lee et al., in J. Vet. Sci (2009) p. 299-304 (DOI: 10.4142/jvs.2009.10.4.299). The normal cells and cancerous cells of the lung are only an example in this context.

In a preliminary investigation, cells from different organ regions and environments of, for example, a patient's organ to undergo surgical operation can be removed and investigated spectroscopically and classified by the histopathologist. These cells and the associated spectra accordingly serve as reference cells, or respectively reference spectra. The spectra can be significantly modulated by an extraordinary number of circumstances, and a timely investigation of reference cells/reference tissue from the patient is therefore desirable. By using absorption spectra which are for example obtained during surgical operation, and by using the reference spectra, conclusions can be made about the composition of the investigated sample (e.g., tissue). In particular, the investigated tissue can be classified as cancerous, or respectively not cancerous.

FIG. 3 shows a measuring probe according to a first example, and an example of an arrangement for measuring spectral absorption comprising the measuring probe. The measuring probe has an elongated shape (such as a needle or catheter shape) with a longitudinal axis La. The longitudinal axis La corresponds at least approximately to the infeed direction of the measuring probe.

The arrangement for measuring spectral absorption comprises a light source 1. The light source 1 can be or can comprise a brilliant, broadband light source with a continuous or discreet spectrum, a tunable light source, a light source with an addressable spectrum, or another suitable light source. Furthermore, the light source can comprise a filter and/or a light modulator. Preferably, the intensity of the light source is selected such that reliable measuring results can be provided without destroying the investigated sample (in this example, the tissue 16) during the measuring process. The light source 1 can emit light in the MIR range, for example at approximately 6 µm to approximately 11 µm. Other spectral ranges are also possible.

The light emitted by the light source is coupled into a fibre 4 with a fibre core 3 and a fibre core end 5, and is conducted to the measuring probe. Special fibres can be used for medium infrared such as silver halide fibres. The outer diameter of the fibres can for example be between 0.5 mm and 1 mm, preferably 0.9 mm or smaller. The core of the fibre can be approximately 0.1 mm. The fibre 4 can be a monomode or non-monomode fibre. The use of a non-monomode fibre can be advantageous to suppress parasitic interference.

In the example shown in FIG. 3, the fibre 4 is both part of the illumination channel as well as part of the detection channel so that both the illumination light as well as the measuring light to be detected after measurement is propagated through the fibre 4. The one fibre version has the advantage that it is constructed the thinnest (e.g., knitting needle) and is consequently minimally invasive. One disadvantage of this solution can be the reflection problem at the transition surfaces (e.g., from an optically thin to an optically dense material and vice versa). In an application to measure the absorption spectra of aqueous samples such as tissue samples, the attenuation of the beamed-in light is very strong due to the thin water film in freshly cut tissue; hence undesirable front reflection can be 100 times greater than the remaining light to be evaluated which comes from the tissue after reflection. Preferably, the optical system of the measuring probe is designed so that none, or only a slight amount, of the directly reflected light not propagated through the sample slice re-enters the fibre 4.

One option for minimizing undesirable direct reflection is to AR-coat the refractive surfaces. This could however be problematic in particular with optical elements made of diamond since providing an anti-reflective coating on diamond is very difficult or only feasible with radioactive poisonous substances, which rules out applications of the measuring probe in medicine. Another option is to arrange the refractive surfaces at a sufficient angle with reference to the incident light so that direct reflection does not return into the fibre 4, or respectively into the detection channel. In addition or alternatively, it is also possible to use diffractive optical elements (DOE).

The measuring probe comprises a lens 6, such as an aspherical lens 6 with a free-form surface 7. The aspherical lens 6 can be for example of ZnSe or another suitable transparent material. In the example shown in FIG. 3, the free-form surface 7 is the light entry surface (entry surface) for the aspherical lens 6. The free-form surface can however be a different surface, such as the light exit surface (exit surface) of the aspherical lens 6. The ray bundle which leaves the lens 6 and is incident on the entry surface 8 of the window element 10 is preferably substantially parallel and has a diameter of for example 0.8 mm. The angle of incidence of the ray bundle at the entry surface 8 can be selected depending on the specific geometry of the optical system. In the example shown in FIG. 3, the angle of incidence of the parallel ray bundle at the entry surface 8 is approximately 43°; other values are also possible. A compensation diffraction grating 11 is arranged on the entry surface 8. The compensation diffraction grating 11 can for example be a blazed diffractive transmission diffraction grating with a written-in corrective phase function which is designed to achieve achromatism of the optical system of the measuring probe in a specific spectral range. This makes it possible to return almost all the radiant energy into the fibre core 3. Preferably, the compensation diffraction grating 11 is designed for the first (m=1 or m=−1) order of diffraction; it can, however, be designed for a different order of diffraction.

Furthermore, the measuring probe comprises a cutting apparatus with a first cutting blade 13 and a second cutting blade 17, wherein the two blades form the tip of the measuring probe. The first blade is an integral component of the window element 10 formed from diamond (i.e., the first blade 13 and the window element 10 form a diamond monolith). The second blade 17 is an integral component of the end reflector support element 18 which is formed from a suitable hard material (such as a suitable hard metal). The two blades 13 and 17 are arranged at a distance from each other so that a "throat", or respectively a gap is formed whose constituent element is the measuring gap 12. The width 12A of the "throat", or respectively gap, is preferably variable. Accordingly as described above, the "throat" can be opened, or respectively closed before and after a spectral measurement. The "throat" terminates in the sample entry 14 which simultaneously constitutes the entry of the "throat", or respectively the measuring gap 12.

The end reflector support element 18 is designed movable with reference to the window element 10. In particular, the end reflector support element with the second blade 17 can be moved along the vertical direction (which substantially corresponds to the infeed direction of the measuring probe and the longitudinal axis La of the measuring probe), and/or can vibrate in this direction. In addition, the end reflector support element 18 can optionally be moved along a second axis which is at an angle with reference to the longitudinal axis La, or can vibrate in this direction. The cutting procedure can be supported by the movement of the end reflector supported element 18. In addition, compression of the tissue located in the measuring channel 12 can be achieved to minimize the loss of absorption from water.

The end reflector 19 is arranged on one of the surfaces of the end reflector support element 18. The end reflector 19 constitutes one of the boundary surfaces of the measuring gap 12. On the other side, the measuring gap 12 is bordered by one of the surfaces (window surface 9) of the window element. The end reflector is designed as a reflective diffraction grating such as a microprofiled, blazed reflective diffraction grating, with a written-in lens correction phase function. The end reflector 19 is furthermore designed as a retroreflector and makes it possible to return the radiant energy to the m=−1 order of diffraction. The end reflector 19 can, however, be designed for a different order of diffraction. On the right, FIG. 3 shows an enlarged view of the end reflector (not to scale) and the ray path through the end of reflector 19 (see FIG. 3, detail A).

The measuring gap 12 is arranged at an angle to the longitudinal axis La of the measuring probe. The infeed direction of the measuring probe into the tissue to be measured (analysed) and the gap direction preferably enclose an angle of at least 3° (5°) degrees, and typically an angle of 20° to 50°. In the depicted example, the measuring gap 12 is parallel. The measuring gap 12 can however be wedge-shaped, wherein the wedge angle is preferably an average wavelength (lambda average) over the gap length.

The angled, preferably parallel measuring gap 12 has the advantage that, given an oscillating up-and-down movement of the end reflector support element 18 with the second blade 17, compression of the cut-off tissue can be achieved by pressure. Preferably, the cut-off tissue is compressed to approximately 5 µm to 10 µm in order to minimize the loss of absorption from water. Greater thicknesses are, however, also possible, in particular when the intensity of the measuring light is greater. The angled parallel gap furthermore has the advantage that measured tissue can be discarded as needed on the side through the disposal channel 21. The advantage is that the measuring probe can be designed more compact, or respectively smaller. The width of the measuring gap 12A is variable such that compression of the sample slice located in the measuring gap 12 can be achieved.

For in vivo measurement, the measuring probe 12 is first introduced into the depth of the sample 16 (e.g., into the depth of an organ, or respectively the tissue) (puncture process). The puncturing by the measuring probe preferably occurs at an at least approximately constant speed, such as approximately 0.1 mm/s to 0.5 mm/s. Preferably, the measuring probe is introduced by means of a precision robot arm into the organ, or respectively into the tissue 16. This allows the required precision, exertion of force and constant speed of the downward movement to be ensured. The puncture process can, however, also occur manually. Whether or not it is possible to manually introduce the measuring probe depends for example on the respective organ and patient situation.

After the measuring probe has penetrated to the desired measuring point, the measuring process is started. The position of the measuring probe 12 with reference to the investigated organ during the puncture process can be determined using previously ascertained data with reference to the spatial orientation of the patient's body and/or the investigated organ. In addition or alternatively, the position of the measuring probe in the investigated organ can be measured using suitable measuring procedures (e.g., CT, ultrasound, etc.), preferably in real time, and possibly depicted on a suitable display. With reference to the data on the position of measuring probe, the measuring procedure can be started and/or ended.

By means of the cutting apparatus integrated in the measuring probe (comprising blades 13 and 17), a tissue slice or respectively flap (sample slice) can be cut off and conveyed into the measuring channel 12. Then the tissue located in the measuring channel 12 can be compressed. This can be achieved by microvibrations of the end reflector support element 18. The spectral absorption is preferably measured directly after the cutting process and the optional compression of the tissue.

During the measuring process, the substantially parallel measuring ray bundle is coupled by the window element 10 into the measuring gap 12 and coupled out of the measuring gap 12 after it passes twice through the tissue located in the measuring gap. At least a majority of the parallel measuring ray bundle passes, preferably obliquely, through the window surface 9 of the window element 10. The measuring light propagates through the tissue located in the measuring gap 12, is reflected by the end reflector 19, and propagates a second time through the tissue located in the measuring gap 12. The end reflector 19 is designed and arranged so that at least the majority of the measuring light returns into the fibre 4 after being reflected and passing twice through the measuring gap 12. By means of the beam divider 2 and, if applicable, suitable deflection and/or focusing optics, the measuring light is guided to the apparatus for spectral analysis 22. By using a collimated bundle with a small diameter which is reflected back into itself by the end reflector 19, in particular in combination with confocal discrimination as the measuring light enters into the fibre end 5, undesirable scattered light can largely be suppressed. In particular, Mie scattering effects can be significantly reduced.

After measuring, the measured tissue is conveyed into the discharge or disposal channel 21. The disposal channel 21 terminates, or respectively is in connection with, the output of the measuring channel (sample outlet) 20. The measured tissue can for example be conveyed into the disposal channel 21 and out of the disposal channel 21 by means of a suction device (not shown), perhaps supported by micro-vibrations. If it is unnecessary to perform an additional histological investigation of the tissue measured spectrally in situ, it is possible to omit the disposal channel, which has the advantage that the measuring probe can be constructed thinner and hence more patient-friendly. The tissue which has already been measured spectrally can in this case be destroyed, for example by means of high-energy fs laser pulses. The killed tissue can then be discarded or released to the bodily tissue where it is absorbed. The high energy fs laser pulses are guided, preferably at a delay, through the same fibre 4 to spectrally measure the tissue which has already been measured.

The apparatus for spectral analysis 22 comprises a detector such as an integral detector. For the IR range, the detector can for example be a mercury/cadmium/telluride detector which is cooled with liquid nitrogen. The spectral recording time per measuring site in measuring mode is preferably as short as possible, and preferably lies below 1 s to 10 s. During the measuring process, the tissue may not be destroyed too quickly by the radiation load introduced while measuring absorption, i.e. not before it has supplied its spectral signature. To enable reliable measurements within the short period, the light source can be a brilliant, broadband light source such as a brilliant light source in the MIR range.

FIG. 4 shows a measuring probe according to a second example, and an example of an arrangement for measuring spectral absorption comprising the measuring probe. The optical arrangement of the measuring probe, or respectively the arrangement for measuring spectral absorption, largely corresponds to the optical arrangement of the measuring probe shown in FIG. 3, or respectively the arrangement for measuring spectral absorption, with the difference that the compensation diffraction grating 11 is arranged on the exit surface of the aspherical lens 6. The exit surface of the lens 6 in this example is a curved surface such as a spherical or aspherical (e.g., a free-form) surface. Like the example shown in FIG. 3, the compensation diffraction grating 11 can be a blazed diffractive transmission diffraction grating with a written-in corrective phase function to achieve achromatism.

The ZnSe lens 6 can be processed with a single point diamond. This also applies to the production of the compensation diffraction grating on the ZnSe lens. Accordingly, expensive and complex application of the compensation diffraction grating on the window element made of diamond can be avoided. With regard to undesirable chromatic transverse splitting within the measuring gap 12, it is advantageous to arrange the compensation diffraction grating 11 as close as possible to the measuring gap 12.

FIG. 5 shows a measuring probe according to a third example, and an example of an arrangement for measuring spectral absorption comprising the measuring probe. As in the first and second example, the arrangement for measuring spectral absorption comprises a light source which, in this example, is a brilliant MIR broadband source 32. Furthermore, the arrangement for measuring spectral absorption comprises a Michelson interferometer 23 as a modulator, wherein the interferometer 23 is downstream from the MIR broadband source 32. The light source can, however, be a different light source, such as a light source with a tunable wavelength (e.g., a QCL laser).

As in the above examples, the modulated illumination light is coupled into a fibre 4 and guided to the measuring probe, or respectively to the window element 10.

The window element 10 (not depicted true to scale) is designed as a substantially plane-parallel diamond piece which forms a diamond monolith together with the first blade 13. The compensation diffraction grating 11 is arranged on the entry surface 8 of the window element 10. The compensation diffraction grating 11 is a transmission diffraction grating which is designed to achromatise the optical system.

The measuring probe furthermore comprises an end reflector support element 18, in this case in the shape of a plane-parallel piece with an integrated second blade 17. The end reflector support element 18 can also be made from diamond. It is, however, possible to make the end reflector support element 18 from a different, suitable, preferably hard material. The end reflector support element 18 also forms a monolith with the second blade 17.

The measuring gap 12 is bordered by the substantially flat window surface 9 of the window element 10 and a substantially flat surface of the end reflector support element 18. The end reflector 19 is arranged on the surface of the end reflector support element 18 facing the measuring gap. The end reflector can, as described above, be a diffractive optical element, such as a microprofiled reflection diffraction grating in autoreflection mode, or respectively quasi-autoreflection mode. The diffractive optical element has a phase function which is chosen to achieve achromatism. The diffractive optical element can be a buried diffractive optical element (see FIG. 5, detail A). This has the advantage that the wall bordering the measuring gap 12 is smooth, which can facilitate the conveyance of the tissue into and out of the measuring 12.

The functioning of the measuring probe and the arrangement for measuring spectral absorption according to the third example is similar to the functioning of the example depicted in FIG. 3 with the difference that the measuring ray bundle is not collimated. The divergent ray bundle coming from the end of the fibre falls on the entry surface 8 with the compensation diffraction grating of the window element 10, is diffracted, propagates through the coupling-in and coupling-out element, and is coupled into the measuring gap 12 through the window surface 9 of the window element 10. After being reflected at the end mirror 19, the measuring light again propagates through the measuring gap 12 and is coupled into the fibre 4. By means of the beam divider 2, the measuring light is guided to the detector 30 (as a part of the apparatus for spectral analysis). For the light in the MIR range, the detector can be a mercury/cadmium/telluride detector which is cooled with liquid nitrogen. The detected measuring signal is then analysed to obtain information about the investigated tissue.

Figure 6A:
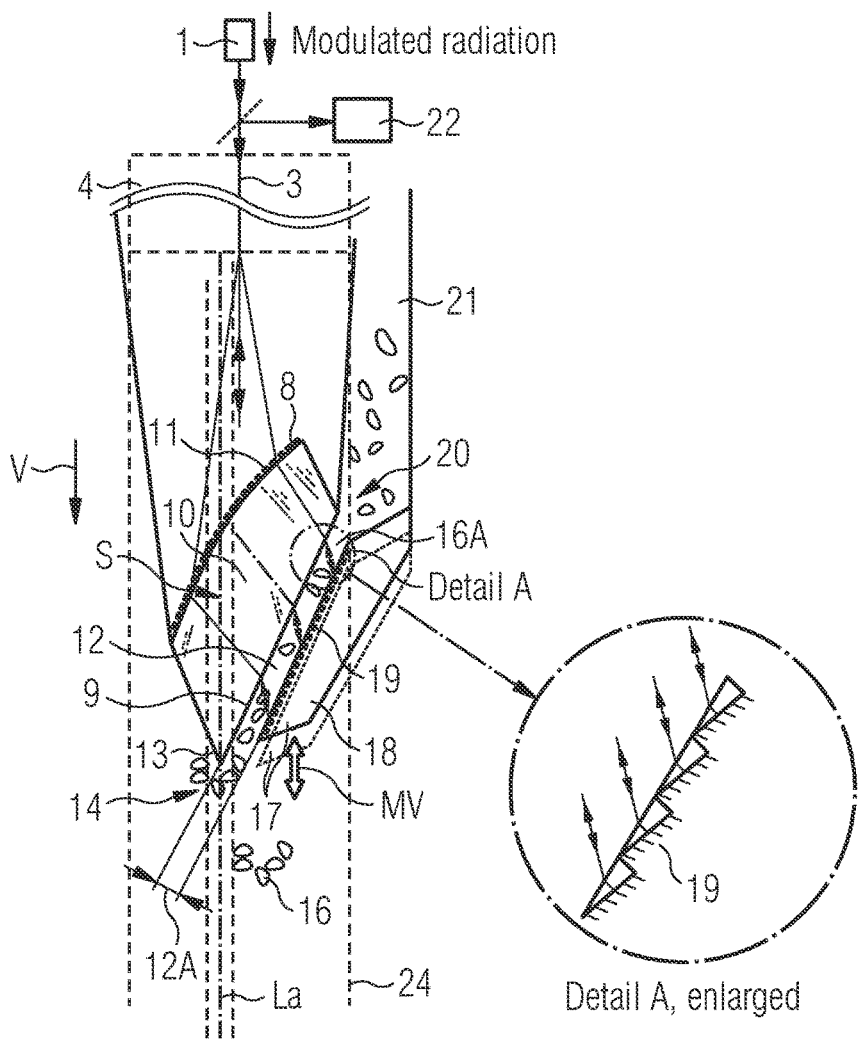

FIG. 6A shows a measuring probe according to a fourth example, and an example of an arrangement for measuring spectral absorption comprising the measuring probe. As with the previous examples, the arrangement for measuring spectral absorption comprises a light source 1 and an apparatus for spectral analysis 22, wherein the light emitted by the light source 1 and optionally modulated is coupled into a fibre 4. The divergent ray bundle coming from the core 3 of the fibre 4 falls on the curved (spherical or aspherical) entry surface 8 with the compensation diffraction grating 11 of the window element 10. The entry surface 8 and the compensation diffraction grating 11 are designed so that the ray bundle S diffracted at the entry surface 8 is at least approximately collimated. The window element 10 made of diamond furthermore has a window surface 9 through which the collimated ray bundle S is coupled into the measuring gap 12. The measuring gap 12 is furthermore bordered by the end reflector 19 which is arranged on a runner-shaped end reflector support element 18. As described above, the end reflector 19 can be designed as a diffractive optical element, preferably as a buried diffractive optical element (see FIG. 6A, detail A, enlarged). The end reflector can work in an autoreflection mode, or in a quasi-autoreflection mode.

Figure 6B:
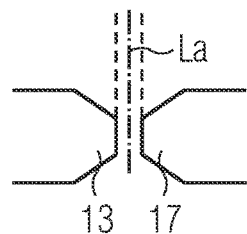

The measuring probe furthermore has two blades 13 and 17 which form the tip of the measuring probe, wherein the first blade 13 is formed integrally with the window element 10, and the second blade 17 is formed integrally with the end reflector support element 18. The first blade 13 in this example is the primary blade and makes the first incision. The second blade 17 is the secondary blade. FIG. 6B shows an enlarged view (not true to scale) of the two blades which form the tip of the measuring probe.

The end reflector support element 18 can be moved along the infeed direction V of the measuring probe (which is substantially parallel to the longitudinal axis La of the measuring probe), or respectively can vibrate along this direction. The end reflector support element 18 can optionally vibrate along a second direction which is oblique (such as perpendicular) to the infeed direction. The cutting process can be supported by the vibration of the end reflector support element 18 with the second blade 17. Furthermore, the width 12 of the measuring gap 12 can be varied in order to achieve a thinning, or respectively compression, of the tissue located in the measuring gap.

Furthermore, the measuring probe comprises a compensation diffraction grating 11 which is arranged on the entry surface 8 of the window element 10. The compensation diffraction grating 11, in combination with the diffractive end reflector 19, is designed to achieve achromatism of the optical system. The remaining elements as well as the functioning of the measuring probe and the arrangement for measuring spectral absorption in this example largely correspond to the functioning of the example shown in FIG. 3.

In the examples shown in FIGS. 3 to 6, the end reflector 19 simultaneously constitutes one of the surfaces bordering the measuring gap 12. Expressed otherwise, the end reflector 19 is designed as a front end reflector. The end reflector support element 18 consequently does not have to be transparent and can be formed from any suitable material. Since the end reflector support element 19 does not have to possess any transmission and/or fibre connection, the end reflector support element 18 is suitable for being designed as a vibration microtome. In this case, the end reflector support element 18 can be securely or firmly connected to the second blade 17 and, for example, vibrate in the longitudinal direction of the measuring probe (up and down).

Figure 7A:
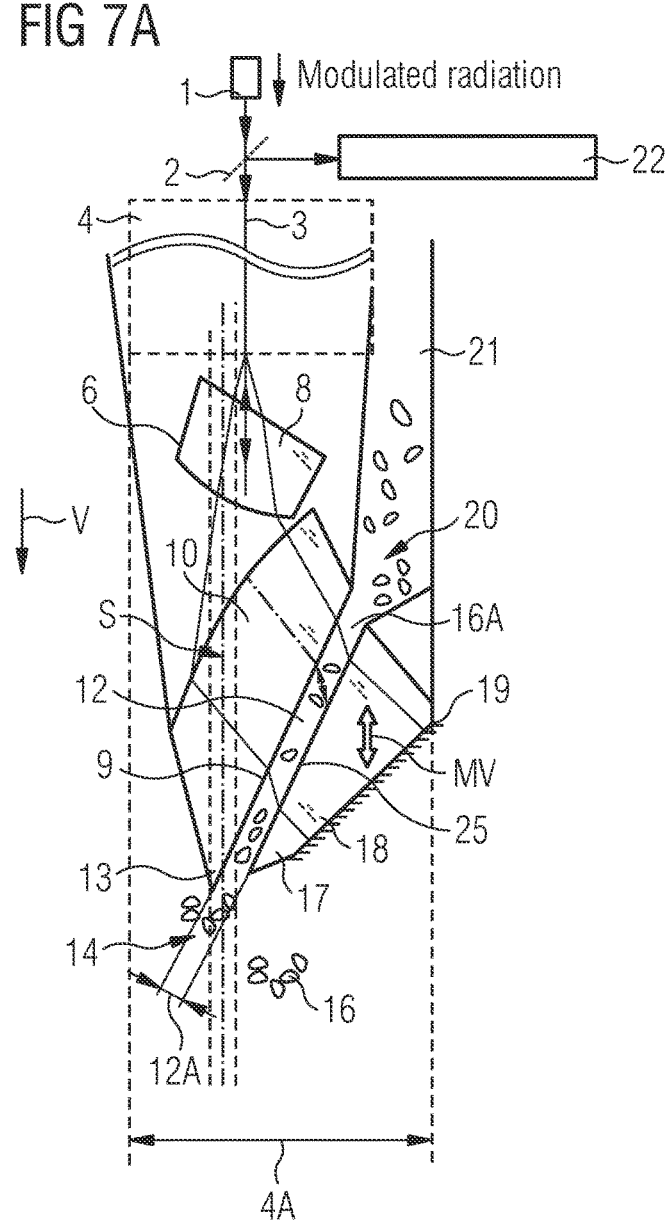

It is, however, possible to arrange the end reflector 19 as a rear end reflector. FIG. 7A shows a measuring probe with a rear end reflector according to a fifth example, and an example of an arrangement for measuring spectral absorption comprising the measuring probe. As with the previous examples, the arrangement for measuring spectral absorption comprises a light source 1 and an apparatus for spectral analysis 22, wherein the light emitted by the light source 1 is coupled into the fibre core of a fibre 4.

Figure 7B:
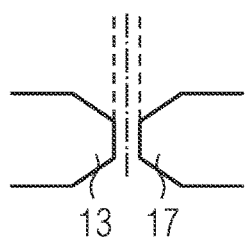

The measuring probe comprises an e.g. aspherical lens 6 made of ZnSe, or a different suitable transparent material. Furthermore, the measuring probe comprises a window element 10, preferably made of diamond, and an end reflector support element 18 which also is made of a transparent material, preferably diamond. The window element 10 is formed integrally with the first blade 13 (i.e., the first blade 13 and the window element 10 form a monolith). Likewise, the end reflector support element 18 is formed integrally with second blade 17. The first blade 13 in this example is the primary blade and makes the first incision. The second blade 17 is the secondary blade. FIG. 7B shows an enlarged view (not true to scale) of the two blades which form the tip of the measuring probe.

The measuring gap 12 is bordered by the substantially flat window surface 9 of the window element 10 and the substantially flat window surface 25 of the transparent end reflector support element 18. The end reflector 19 is arranged on one of the other surfaces of the prismatic or runner-shaped end reflector support element 18. In this example, the end reflector 19 is a mirror, for example made of gold.

The coupling-in and coupling-out element 10 is designed as a spherical or aspherical diamond lens, or a diamond prism (with a diffraction index of n=2.38 at a wavelength of 8.6 µm), and has a curved entry surface 8. The lens 6 and the window element 10 are designed and arranged to collimate the divergent measuring ray bundle coming from the end of the fibre. The collimated measuring ray bundle S is coupled into the measuring gap 12 through the window surface 9, propagates through the measuring gap 12 and through the transparent end reflector support element 18, and is reflected back by the mirror (end reflector) 19. The mirror 19 is arranged so that the measuring light falls substantially perpendicular on the mirror 19 so that the measuring light bundle reflects back into itself. The reflected measuring ray bundle propagates again through the end reflector support element 18, the measuring gap 12 and the window element 10, and is coupled into the fibre 4. By means of the beam divider 2, the measuring light is conducted to the apparatus for spectral analysis.

As in the above examples, the end reflector support element 18 is movable with respect to the window element 10. In particular, the end reflector support element 18 with the second blade 17 can be moved along the vertical direction (which substantially correspond to the infeed direction V of the measuring probe and the longitudinal axis La of the measuring probe), and/or can vibrate in this direction. In addition, the end reflector support element 18 can be moved along a second axis which is at an angle with reference to the longitudinal axis La, or respectively can vibrate in this direction.

The remaining elements as well as the functioning of the measuring probe and the arrangement for measuring spectral absorption (e.g., the sample outlet 20, disposal channel 21, etc.) largely correspond to the elements shown in FIG. 3.

FIG. 8A shows a measuring probe according to a sixth example, and an example of an arrangement for measuring spectral absorption comprising the measuring probe. The optical arrangement of the measuring probe shown in FIG. 8A corresponds to the optical arrangement of the measuring probe shown in FIG. 6A with the difference that the second blade 17 is designed as the primary blade. FIG. 8B shows an enlarged view (not true to scale) of the two blades 13 and 17 which form the tip of the measuring probe.

The second blade 17, which can be moved along the infeed direction V, makes the first incision into the tissue 16 to be investigated followed by the first blade 13. The movable, runner-shaped end reflector support element 18 with the integrally-shaped second blade 17 can be made of diamond or another hard material. Since the end reflector 19 is directly adjacent to the measuring gap 12, the end reflector support element 19 does not have to be transparent.

Figure 9A:
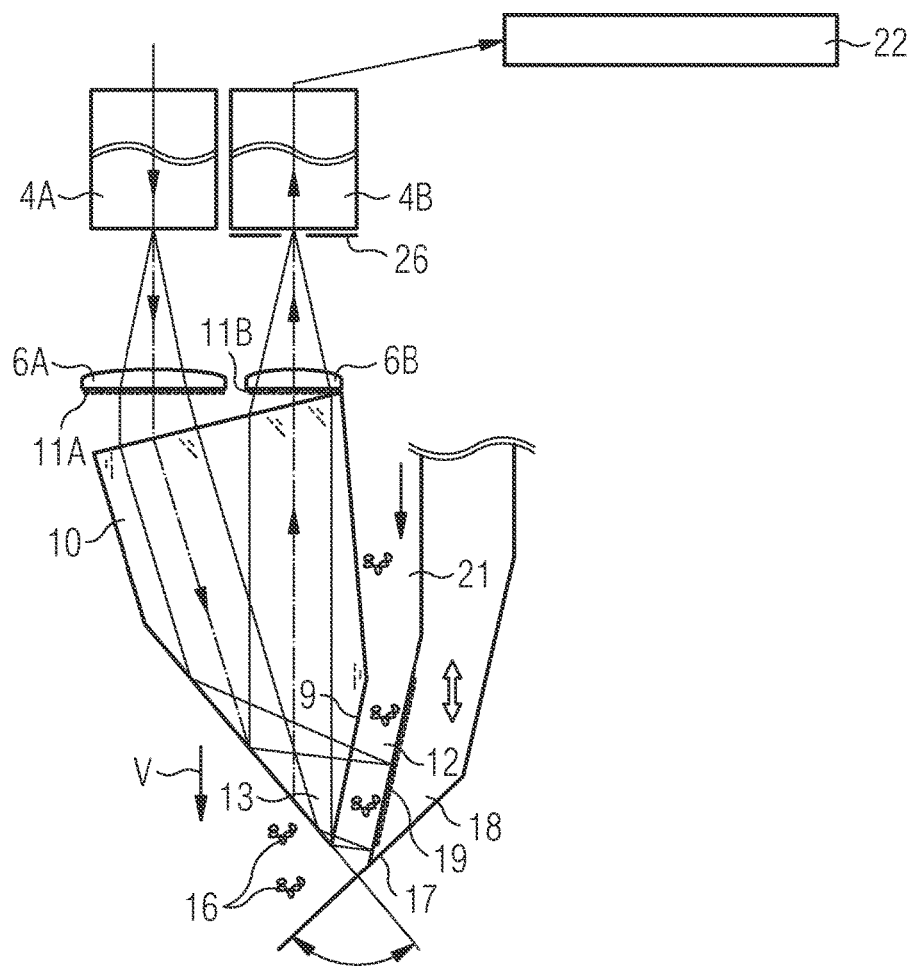
Figure 9B:
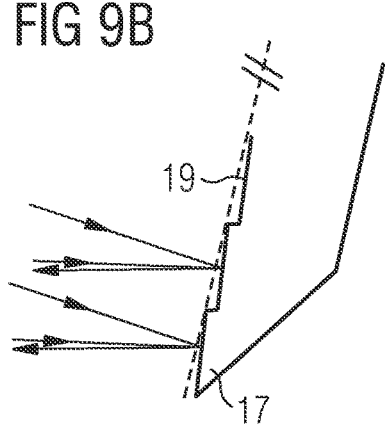

The measuring probes, or respectively arrangements for measuring spectral absorption, shown in FIGS. 1 to 8 each have a fibre 4 which is both a part of the illumination channel as well as part of the detection channel. FIG. 9A shows a measuring probe according to a seventh example and an exemplary arrangement for measuring spectral absorption comprising the measuring probe, wherein the illumination channel and the detection channel of the arrangement for measuring spectral absorption are separate from each other. FIG. 9B shows an enlarged detailed view of a diffractive end reflector 19.

As in the previous examples, the arrangement for measuring spectral absorption comprises a light source (not shown) and an apparatus for spectral analysis 22. The light emitted by the light source is coupled into the fibre core of a transmission, or respectively illumination, fibre 4A. The divergent ray bundle coming from the end of the fibre is collimated by the ZnSe lens 6A and propagated through the window element 10. A first compensation diffraction grating 11A is arranged on the exit surface of the first lens 6A in order to achieve achromatism of the optical system. The compensation diffraction grating 11A can be a blazed transmission grating with a written-in lens and corrective phase function, and possibly a wedge factor. The measuring light is coupled into the measuring gap 12, propagated through the measuring gap 12, reflected by the end reflector 19, again propagated through the measuring gap 12, and is coupled into a detection fibre 4B by means of a second ZnSe lens 6B. Arranged on the light entrance surface of the second lens 6B is a second compensation diffraction grating 11B such as a blazed transmission grating with a written-in lens and corrective phase function, and possibly a wedge factor. Arranged in the focal plane of the second ZnSe lens 6B is a diaphragm 26 which directly hides or blends out reflection. The second compensation diffraction grating 11B is designed to achieve substantial achromatism of the optical system in combination with the first compensation diffraction grating 11A and the end reflector 19 designed as a diffractive optical element.

The measuring probe furthermore has a first blade 13 which is formed integrally with the window element 10, and a second blade 17 which is formed integrally with the movable end reflector support element 18. Furthermore, the measuring probe has a disposal channel 21 which is arranged between the window element 10 and the movable end reflector support element 18, and terminates in the measuring gap 12. The remaining elements and the functioning of the measuring probe and the arrangement for measuring spectral absorption substantially correspond to the elements shown in the previous figures.

FIG. 10 shows a measuring probe according to an eighth example. The measuring probe can move horizontally relative to sample removal, i.e., the infeed direction V is substantially parallel to the horizontal direction. The movement for removing the samples is preferably supported by vibration. The measuring probe comprises an illumination and detection fibre 4, a lens 6 (e.g., a ZnSe lens) for collimating the measuring ray, a window element 10 made of diamond with a first blade 13, and a diffractive end reflector 19. The end reflector is arranged on a movable end reflector support element 18 which forms a monolith with the second blade 17. Furthermore, the measuring probe comprises a removal channel 21 which is connected to a suction device (not shown). The remaining elements and the functioning of the measuring probe and the arrangement for measuring spectral absorption substantially correspond to the elements shown in the previous figures.

FIG. 11 shows a measuring probe according to an ninth example. The measuring probe comprises an illumination and detection fibre 4, a lens 6 (e.g., a ZnSe lens) for collimating the measuring ray a window element 10 made of diamond, and a diffractive end reflector 19. The end reflector is arranged on a movable end reflector support element 18 which forms a monolith with a first blade 13. The end reflector support element 18 is movable along the infeed direction V, wherein the movement of the end reflector support element is supported by vibration. The sample can be a tissue sample which comprises an aqueous medium 16a and a sample particle (e.g., tissue particle). The sample slice to be measured is removed in this example by an upward movement of the end reflector support element with the second blade 13. The remaining elements and the functioning of the measuring probe and the arrangement for measuring spectral absorption substantially correspond to the elements shown in the previous figures.

Figure 12:
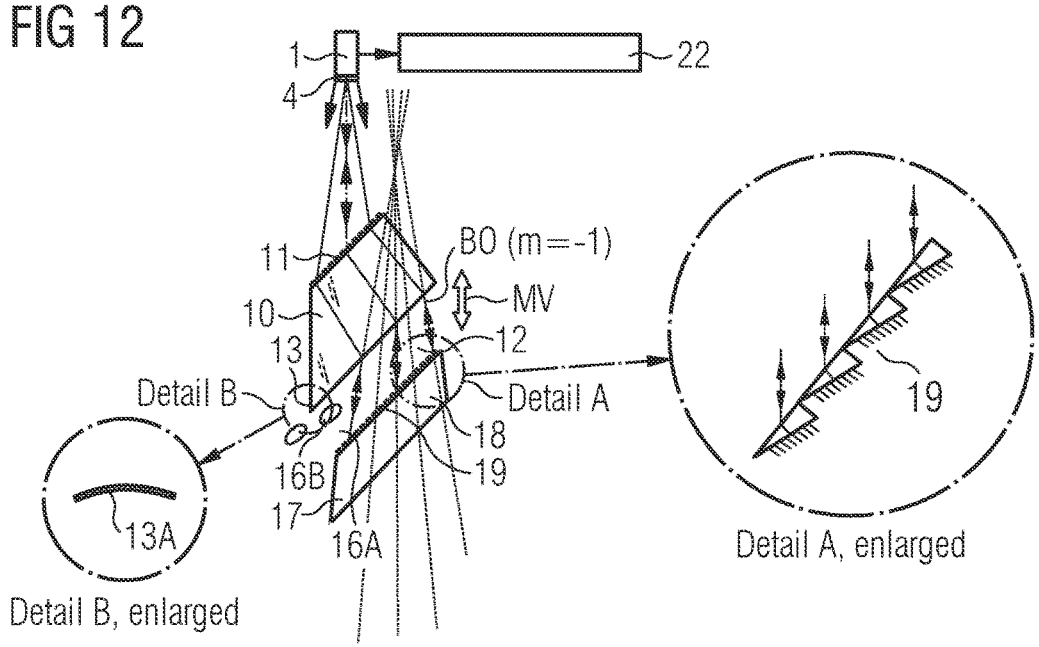

FIG. 12 shows a measuring probe according to a tenth example, and an example of an arrangement for measuring spectral absorption comprising the measuring probe. The arrangement for measuring spectral absorption comprises a light source 1 with a fibre outlet and an apparatus for spectral analysis 22. The light emitted by the light source is coupled into a fibre 4 and guided to the measuring probe. The measuring probe comprises a window element 10 (for example made of diamond) with the first blade 13 and a compensation diffraction grating 11. The cutting edge of the first blade 13 can, if applicable, be slightly hollow (see FIG. 12, detail B, enlarged). Furthermore, the measuring probe comprises a movable (preferably supported by vibration) end reflector support element 18 made of hard material, or respectively a material with a second blade 17 and a diffractive end reflector 19. The diffractive end reflector 19 is for example a buried diffractive optical element which is designed for reflection within the m=−1 order of diffraction. The end reflector 19 is designed for retroreflection, or respectively quasi-retroreflection, so that illumination light and the measuring light have a common ray path after passing twice through the sample slice. It is accordingly possible to build the measuring probes smaller, preferably with a diameter of 1 mm and smaller. The remaining elements and the functioning of the measuring probe and the arrangement for measuring spectral absorption substantially correspond to the elements shown in the previous figures.

Figure 13:
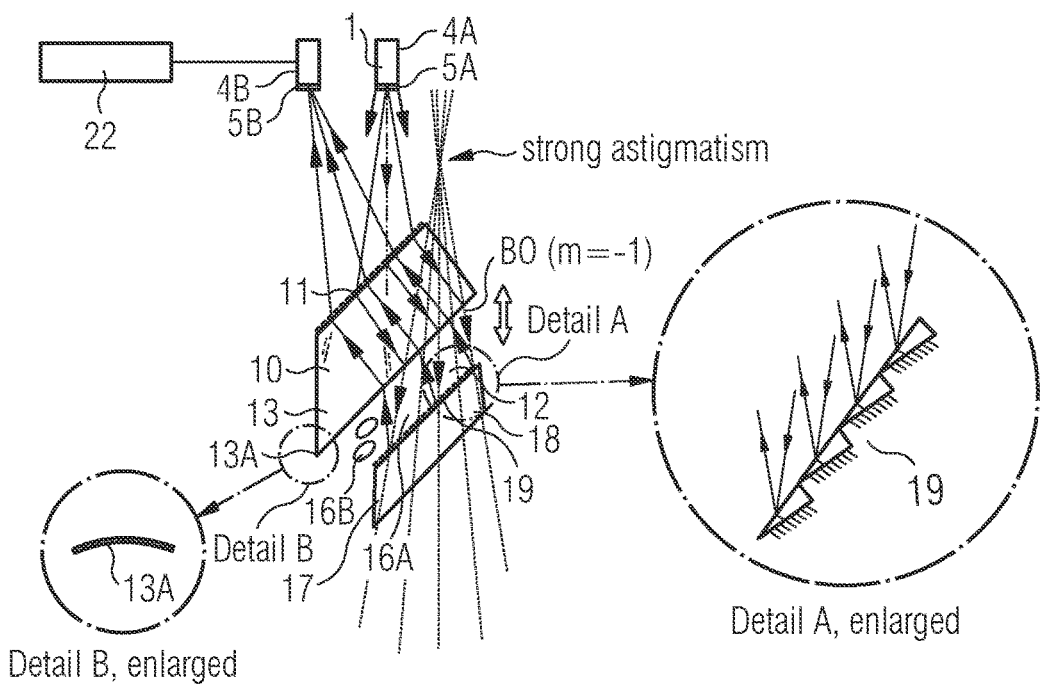

FIG. 13 shows a measuring probe according to an eleventh example, and an example of an arrangement for measuring spectral absorption comprising the measuring probe. As in the example shown in FIG. 9A, the measuring probe, or respectively the arrangement for measuring spectral absorption, comprises a separate illumination and detection channel.

The arrangement for measuring spectral absorption according to the eleventh example comprises a light source 4A with an integrated fibre having a fibre core end 5A, a detection fibre 4B with a fibre input 5B, and an apparatus for spectral analysis 22. The measuring probe comprises a window element 10 (for example made of diamond) with an integrated first blade 13 and a compensation diffraction grating 11. The cutting edge of the first blade 13 can, if applicable, be slightly hollow (see FIG. 13, detail B, enlarged). Furthermore, the measuring probe comprises a movable (preferably supported by vibration) end reflector support element 18 made of hard material, or respectively a material with an integrated second blade 17 and a diffractive end reflector 19. The diffractive end reflector 19 (see FIG. 13, detail A, enlarged) is for example a buried diffractive optical element which is designed for reflection within the m=−1 order of diffraction. The end reflector 19 is designed so that the measuring light is coupled into the detection fibre 4B after passing twice through the sample slice and the window element 10. In this example, the end reflection 19 has strong astigmatism. The remaining elements and the functioning of the measuring probe and the arrangement for measuring spectral absorption substantially correspond to the elements shown in the previous figures (see in particular FIG. 9A).

Figure 14A:
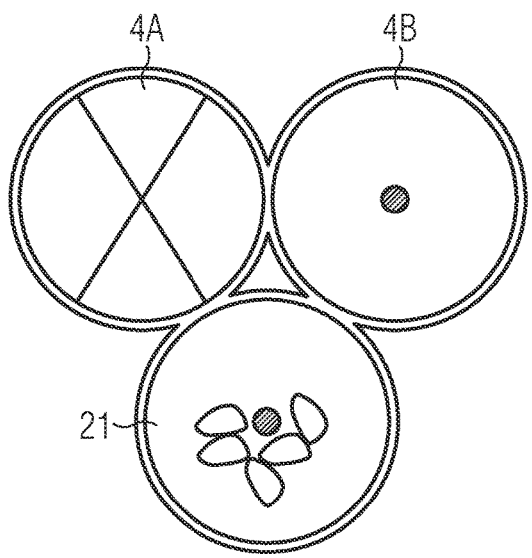
Figure 14B:
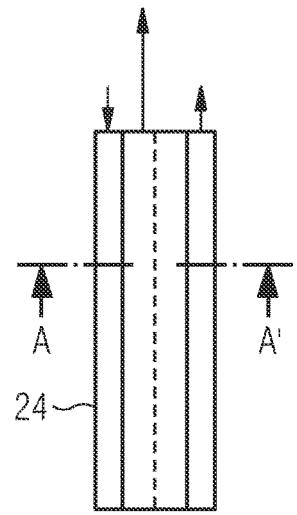

FIG. 14A shows a measuring probe according to a twelfth example, wherein FIG. 14A shows the cross-section of the measuring probe along line A-A', and FIG. 14B shows a side view of the measuring probe (not true to scale).

The measuring probe comprises an illumination fibre 4A, a detection fibre 4B, and a removal channel (discharge or disposal channel) 21 for cut-off tissue after measuring absorption (see FIG. 14A). The illumination fibre 4A, the detection fibre 4B and the disposal channel 21 are integrated in a housing 24 (see FIG. 14B). The housing can for example be made of high-grade steel or another suitable biocompatible material. After measuring absorption, the measured tissue can be suctioned off by a suitable suction device (not shown) through the disposal channel 21, optionally with the support of micro-vibration. If for reasons of space (for example in order to make the measuring probe as thin as possible) the measuring probe is not to have a disposal channel for the measured tissue, the measured tissue, or respectively the measured tissue pieces and/or cells, can be killed by generating heat with fs laser pulses and then released or respectively disposed of into bodily tissue where it is resorbed. The remaining elements and the functioning of the measuring probe and the arrangement for measuring spectral absorption substantially correspond to the elements shown in the previous figures.

Figure 15A:
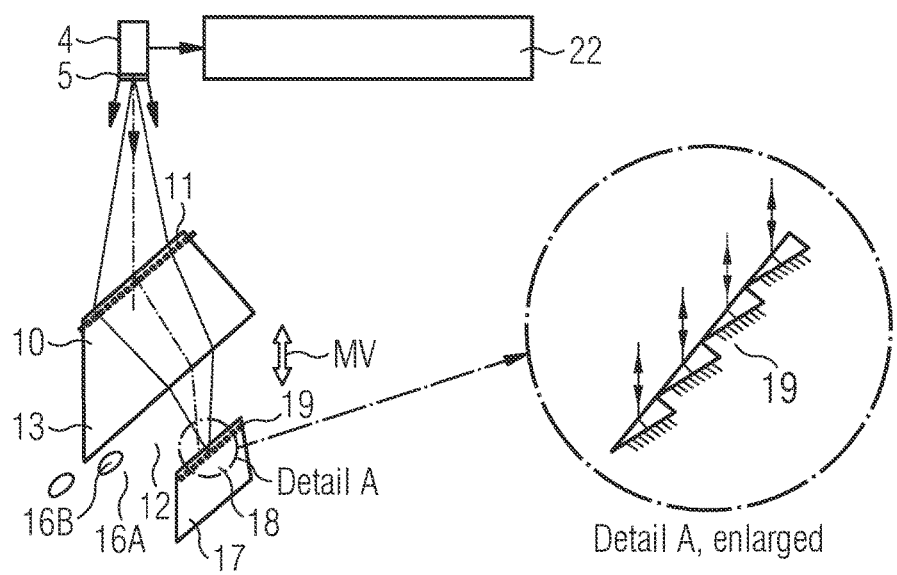

FIG. 15A shows a measuring probe according to a thirteenth example, and an arrangement for measuring spectral absorption comprising the measuring probe. As in the above examples, the arrangement for measuring spectral absorption comprises a light source 1 with an integrated fibre with a fibre core end 5A, and an apparatus for spectral analysis 22. The measuring probe comprises a window element 10 with the first blade 13 and a compensation diffraction grating 11. Furthermore, the measuring probe comprises a movable (preferably supported by vibration) end reflector support element 18 made of hard material, or respectively a material with a second blade 17 and a diffractive end reflector 19 which is designed for retroreflection, or respectively quasi-retroreflection. In this example, a focused, or respectively converging measuring ray is used. The focus diameter is for example approximately 200 μm; other values are also possible. Due to the relatively large detection aperture angle, this optical arrangement has relatively high efficiency during detection. The intensity of the illumination light can be relatively low given the relatively small measuring field. The remaining elements and the functioning of the measuring probe and the arrangement for measuring spectral absorption substantially correspond to the elements shown in the previous figures.

In the examples shown in FIGS. 3 to 15, the measuring gap 12 is arranged obliquely to the longitudinal axis La of the measuring probe. FIGS. 16 to 19 show examples of arrangements for measuring spectral absorption with measuring probes in which the measuring gap 12 is arranged substantially parallel to the longitudinal axis La of the measuring probe.

Figure 16A:
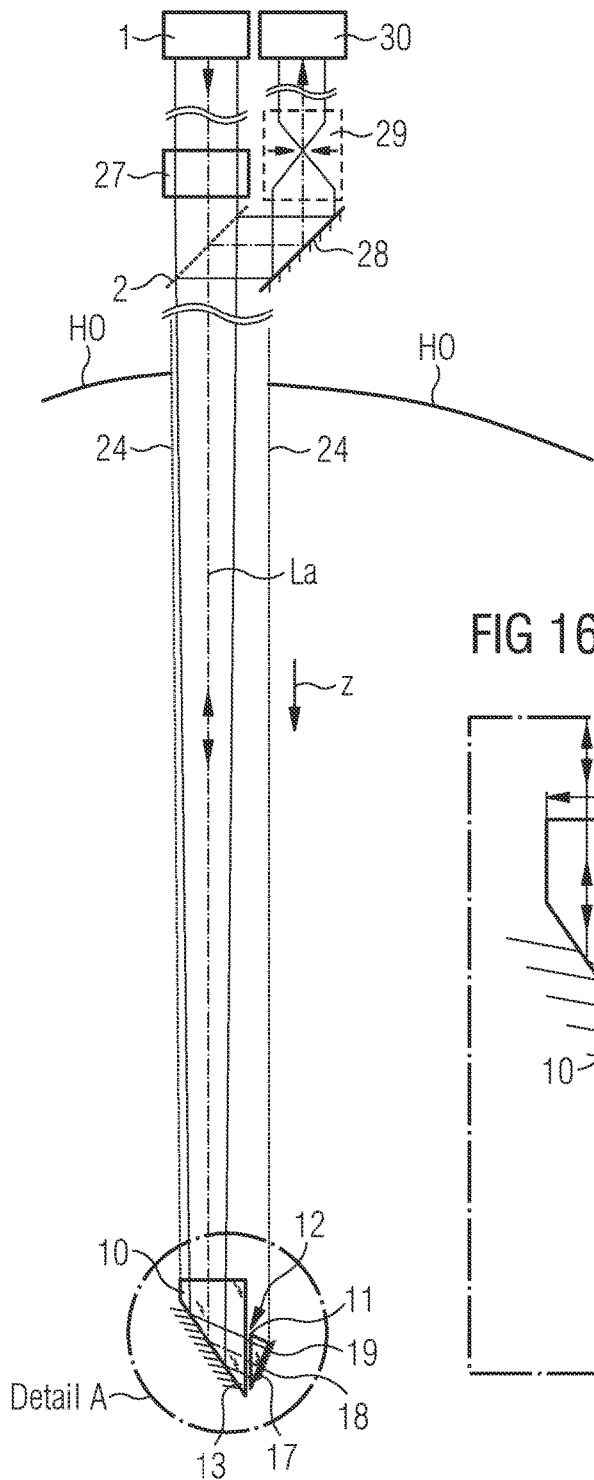
Figure 16B:
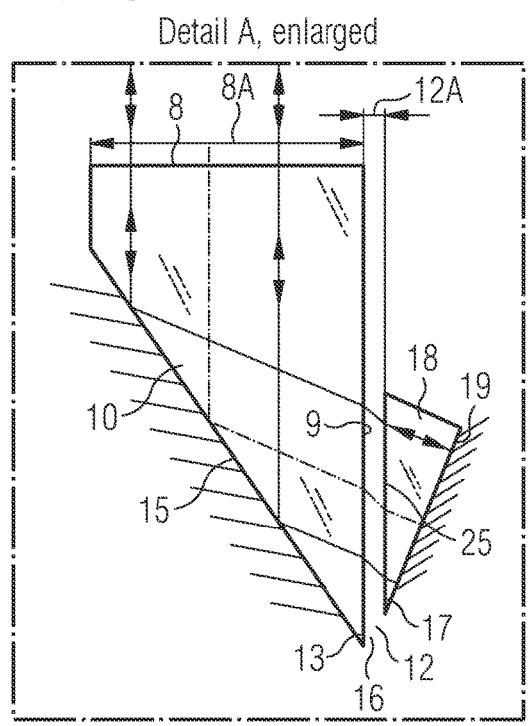

FIG. 16 shows a measuring probe according to a fourteenth example and an arrangement for measuring spectral absorption comprising the measuring probe, wherein FIG. 16A shows an overview of the arrangement for measuring spectral absorption with the measuring probe; FIG. 16B shows an enlarged representation of the front part of the measuring probe; FIG. 16C shows a schematic view of the front part of the measuring probe in a first position during the cutting process, and FIG. 16D shows a schematic view of the front part of the measuring probe in a second position during the cutting process. In this example, the end reflector is a mirror, such as a gold mirror that is arranged as a rear reflector.

As in the above examples, the arrangement for measuring spectral absorption comprises a light source 1. The light source can for example be a tunable quantum cascade laser battery with a wavelength tuning range of 7 µm to 10 µm. The light emitted by the light source 1 is at least approximately shaped into a parallel measuring ray bundle by means of a ray-forming optical system 27. The measuring ray bundle is coupled into the measuring gap 12 by means of the window element 10 of the measuring probe and is coupled out of the measuring gap 12 after passing twice through the measuring gap 12.

The window element 10 is designed as a diamond prism with a supersharp primary blade 13. The diamond prism accordingly serves both as a window element 10 and as a primary cutting piece. The primary blade 13 has a cutting tip, or respectively a cutting edge 13A with an angle less than 40°. The diamond prism 10 furthermore has an entry surface 8, a mirrored surface 15, and a window surface 9. The entry surface 8 of the window element 10 in this example is a flat surface with a width 8A of approximately 0.8 mm which is arranged perpendicular to the longitudinal axis La of the measuring probe. The window surface 9 is a substantially flat surface which is parallel to the longitudinal axis La of the measuring probe. The window surface 9 constitutes one of the boundary surfaces of the measuring gap.

The measuring probe furthermore comprises an end reflector prism 18 which is also fabricated from diamond. The end reflector prism 18 has a sharp blade 17, in this case designated a secondary blade, and serves both as an end reflector support element as well as a secondary cutting piece. The secondary blade 17 has a cutting tip, or respectively a cutting edge 17A with an angle of 15°. The end reflector prism 18 has a first transparent, substantially flat surface 25 (window surface) which is substantially parallel to the longitudinal axis La of the measuring probe. The end reflector 19 is designed as a rear mirror and is arranged on the surface of the end reflector prism 18 at an angle relative to the longitudinal axis direction La. The end reflector 19 is designed as a retroreflector so that the measuring light contacting the end reflector 19 is reflected back into itself. A cross-section of the end reflector prism 18 with the end reflector 19 (preferably designed as a rooftop) is shown in FIG. 16D on the right (Detail A).

The measuring gap 12 is bordered by the window surface 9 of the diamond prism 10 and the window surface 25 of the end reflector prism 18. In the depicted example, the measuring gap has two boundary walls which are parallel to one another and which are each parallel to the longitudinal axis of the measuring probe. It is, however, also possible to design the measuring gap 12 in the shape of a wedge. The measuring gap can however have a small wedge angle which is preferably an average wavelength (lambda average) over the gap length.

FIG. 16B shows an enlarged view of the front part of the measuring probe and the ray path of the measuring light. In this case, the measuring gap 12 is filled with water to show the ray path which also exists when there is tissue in the measuring gap since the diffraction index of aqueous tissue is very similar to that of water. The collimated measuring ray bundle contacts the entry surface 8 of the diamond prism 10 at a right angle, is reflected by the mirror, or respectively by the mirrored surface 15, and is coupled into the measuring gap 12 through the window surface 9. The measuring light propagates through the measuring gap 12 with the sample slice located in the measuring gap and is reflected back by the end reflector 19. After being reflected by the end reflector, the reflected measuring ray bundle substantially returns into itself, again propagates through the measuring gap 12, is reflected by the mirror 15, and exits the diamond prism 10 as a substantially parallel ray bundle. By means of the beam divider 2 and the deflection optics 28 (e.g., a deflection mirror), the measuring light is coupled into telescopic focusing optics 29 with a confocal slit diaphragm for eliminating interfering light. After the interfering light is filtered out, the measuring light is guided to a detector 30 (as a part of the apparatus for spectral analysis). The detector 30 can for example be a detector for radiation in the medium infrared, such as a mercury/cadmium/telluride detector (MCT). The detected light is analysed using suitable methods.

The end reflector prism 18 with the secondary blade 17 is movable relative to the diamond prism 10 with the primary blade 13. In particular, the end reflector prism 18 can be moved along the infeed direction V of the measuring probe, or respectively along the longitudinal axis La of the measuring probe. The end reflector prism 18 can be guided with a precise positioning system (not shown) with a micro-actuator. For this purpose, corresponding installation space for a positioning system with a micro-actuator system can be provided in the measuring probe, or respectively in the arrangement for measuring spectral absorption.

During the cutting and measuring process, the primary blade 13, or respectively the diamond prism 10 with the primary blade 13, is lowered through the skin surface into the depth of the tissue 16 to be investigated as shown in FIG. 16C. Then the secondary blade 17, or respectively the end reflector prism with the secondary blade 17, is also moved vertically downward and relative to the primary blade 13 in order to cut off a new tissue flap, or respectively a new sample slice. In FIG. 16D, the secondary blade 17 of the end reflector prism 18 is depicted as already being retracted, wherein a new tissue flap piece, or respectively sample slice, was cut off to be measured. The end reflector prism 18 can also execute a comparatively high-frequency micro-oscillating movement MV to support the process of dissecting the tissue sample 16.

The diamond prism 10, the end reflector prism 18 and possibly other elements (e.g., a disposal channel, optical fibre, etc.) are integrated in a housing 24 which is made of a biocompatible material.

Figure 17:
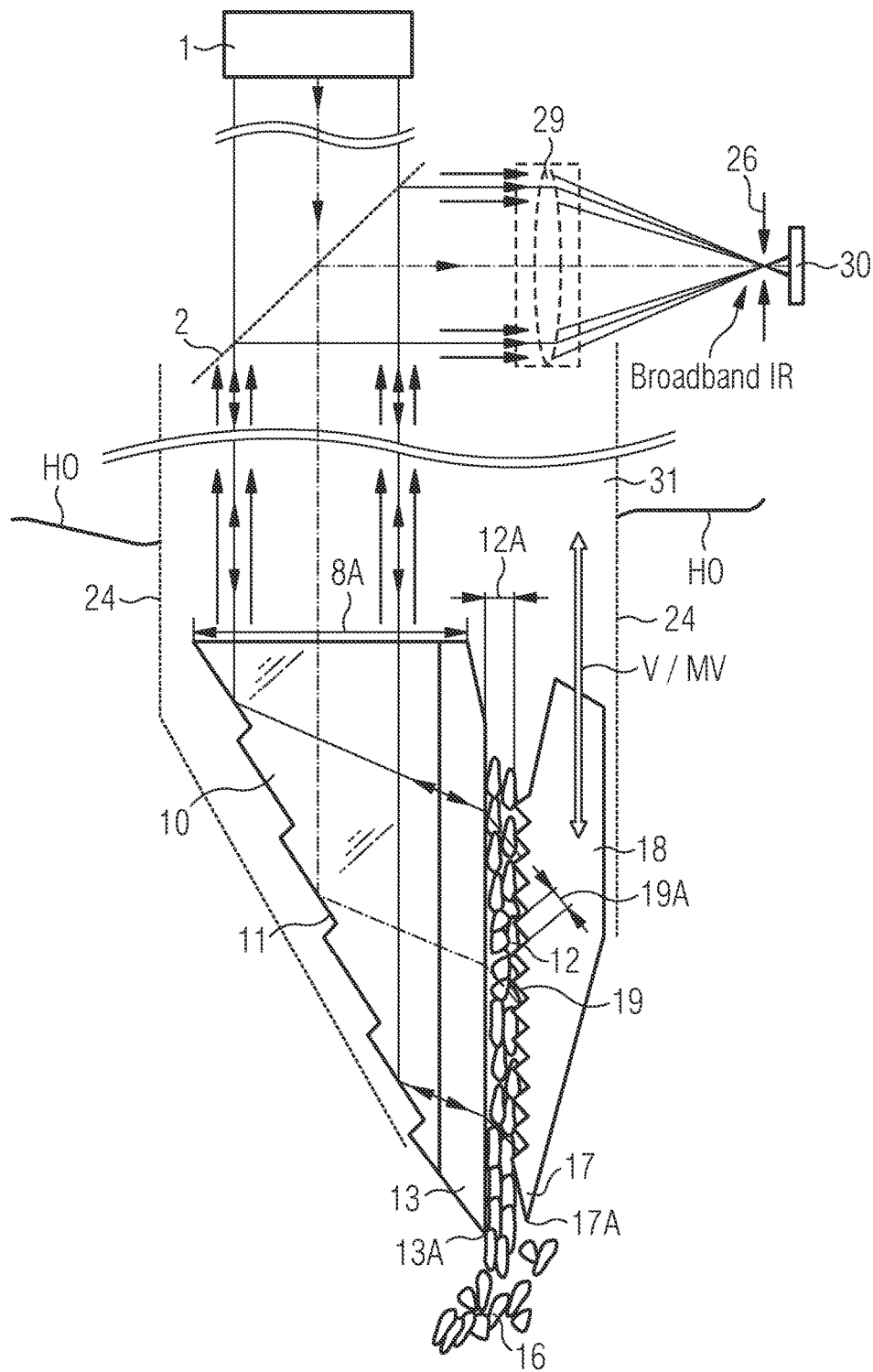

FIG. 17 shows a measuring probe according to a fifteenth example, and an arrangement for measuring spectral absorption comprising the measuring probe. The optical arrangement of the measuring probe, or respectively the arrangement for measuring spectral absorption, largely corresponds to the optical arrangement of the measuring probes shown in FIG. 16, or respectively the arrangements for measuring spectral absorption, with the following differences:

In the example shown in FIG. 17, the end reflector 19 is designed as a blazed reflective diffraction grating with a grating period 19A and a grating height 19B (not shown true to scale in the figures) and is arranged as a front mirror. Furthermore, a blazed reflection grating 11 (compensation diffraction grating) is used instead of the mirror 15. Furthermore, the optical window element 10 is formed from two parts (a ZnSe prism 10A and a second optical element made of diamond 10B) which form a compact optical and mechanical unit, wherein the ZnSe prism 10A is hermetically encapsulated to completely avoid contact with tissue.

The diamond piece 10B has a sharp primary blade 13 which is sharper than 40°. The measuring gap 12 is bordered by one of the flat surfaces of the diamond piece 10B and the flat end reflector 19. The end reflector 19 is designed to let part of the measuring light (e.g., the measuring light refracted in the first order of diffraction) to return into itself approximately at a right angle when the measuring light does not contact the grating surface at a right angle. By using a blazed diffraction grating, the so-called channelled spectrum effect can be specifically reduced.

The reflective diffraction grating of the end reflector 19 can be designed for a first or different order of diffraction (except for the 0-th). The reflective diffraction grating can have a period of approximately 3 μm and a height of approximately 2 μm.

The end reflector 19 designed as a front reflector is arranged on an end reflector support element 18 which for example can be made of a suitable hard material (e.g., diamond), or another suitable material. The end reflector support element 18 with the secondary blade 17 is movable relative to the window element 10 with the primary blade 13, as is the case with the measuring probe shown in FIG. 16. In particular, the end reflector support element 18 can be moved along the infeed direction of the measuring probe, or respectively along the longitudinal axis La of the measuring probe. The end reflector support element 18 can also execute a comparatively high-frequency micro-oscillating movement to support the process of dissecting the tissue. The end reflector support element 18 can e.g. be guided with a precise positioning system (not shown) with a micro-actuator. For this purpose, corresponding installation space 31 for a positioning system with a micro-actuator system can be provided in the measuring probe, or respectively in the arrangement for measuring spectral absorption. The cutting process is carried out as is the case with the measuring probe shown in FIG. 16.

The optical system of the measuring probe is furthermore achromatised by means of the blazed reflection grating 11 (compensation diffraction grating) which is arranged on one of the surfaces of the ZnSe prism 10A. In the process, the compensation diffraction grating 11 is used twice in the ray path. Preferably, the optical system of the measuring probe is achromatised such that the travelling, spectrally broadband measuring ray bundle is effectively collimated for all wavelengths within the tuned spectrum. It is also preferable that the returning measuring ray bundle is also effectively collimated after contacting the grating three times (twice at the compensation diffraction grating 11, and once at the blazed reflective diffraction grating 19). Since the measuring light which leaves the ZnSe prism 10A is at least approximately collimated, a comparatively large amount of the measuring light can pass through the diaphragm 26 (vignetting diaphragm or respectively auxiliary diaphragm) arranged in the focal plane of the achromatic focusing optics 29. The majority of the interfering light is contrastingly filtered out by the diaphragm. This makes it possible to reduce the so-called channelled spectrum effect and the interfering light which distorts the measurements. The filtered measuring light is then detected by an IR detector 30 and then analysed.

The remaining elements and the functioning of the measuring probe and the arrangement for measuring spectral absorption substantially correspond to the elements shown in the previous figures (see in particular FIG. 16).

Figure 18:
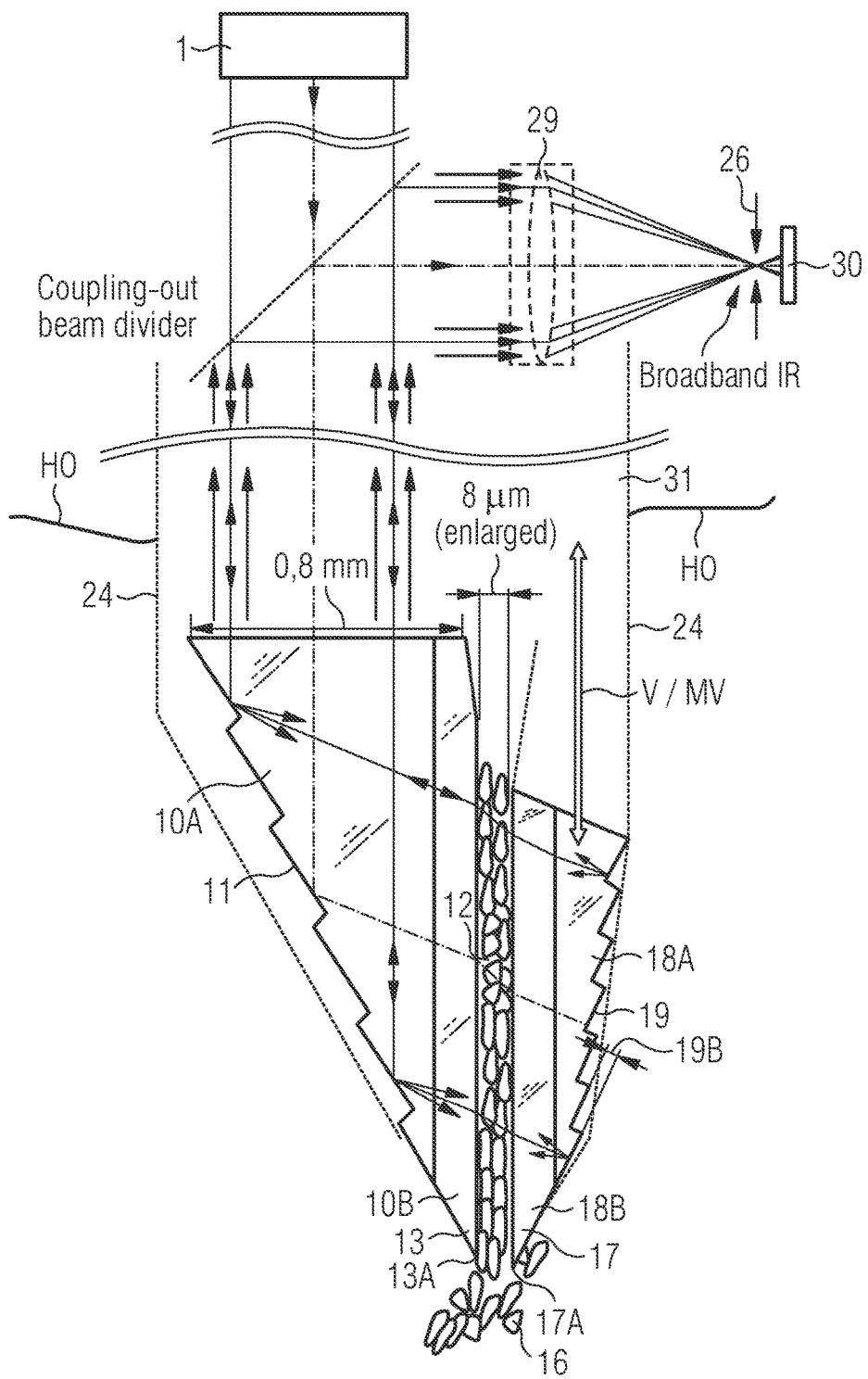

FIG. 18 shows a measuring probe according to a sixteenth example, and an arrangement for measuring spectral absorption comprising the measuring probe. As is the case with the example shown in FIG. 17, the end reflector 19 is designed as a blazed reflective diffraction grating.

The optical system of the measuring probe, or respectively the arrangement for measuring spectral absorption, shown in FIG. 18 substantially corresponds to the optical system of the measuring probe, or respectively the arrangement for measuring spectral absorption, shown in FIG. 17, with the difference that the end reflector is designed as a rear reflector. Furthermore, the end reflector support element 18 is also designed as a diamond piece 18B and ZnSe piece 18A, wherein the diamond piece 18B and the ZnSe piece form a compact optical and mechanical unit. One advantage of ZnSe as the material is that it is transparent to IR measuring light. Furthermore, ZnSe is facile to process which makes it easy to produce a blazed reflective diffraction grating. The ZnSe piece is well encapsulated with a high-grade steel jacket 24 (housing) so that the measuring probe can also be used for in vivo investigations.

The remaining elements and the functioning of the measuring probe and the arrangement for measuring spectral absorption substantially correspond to the elements shown in the previous figures (see in particular FIGS. 16 and 17).

Figure 19:
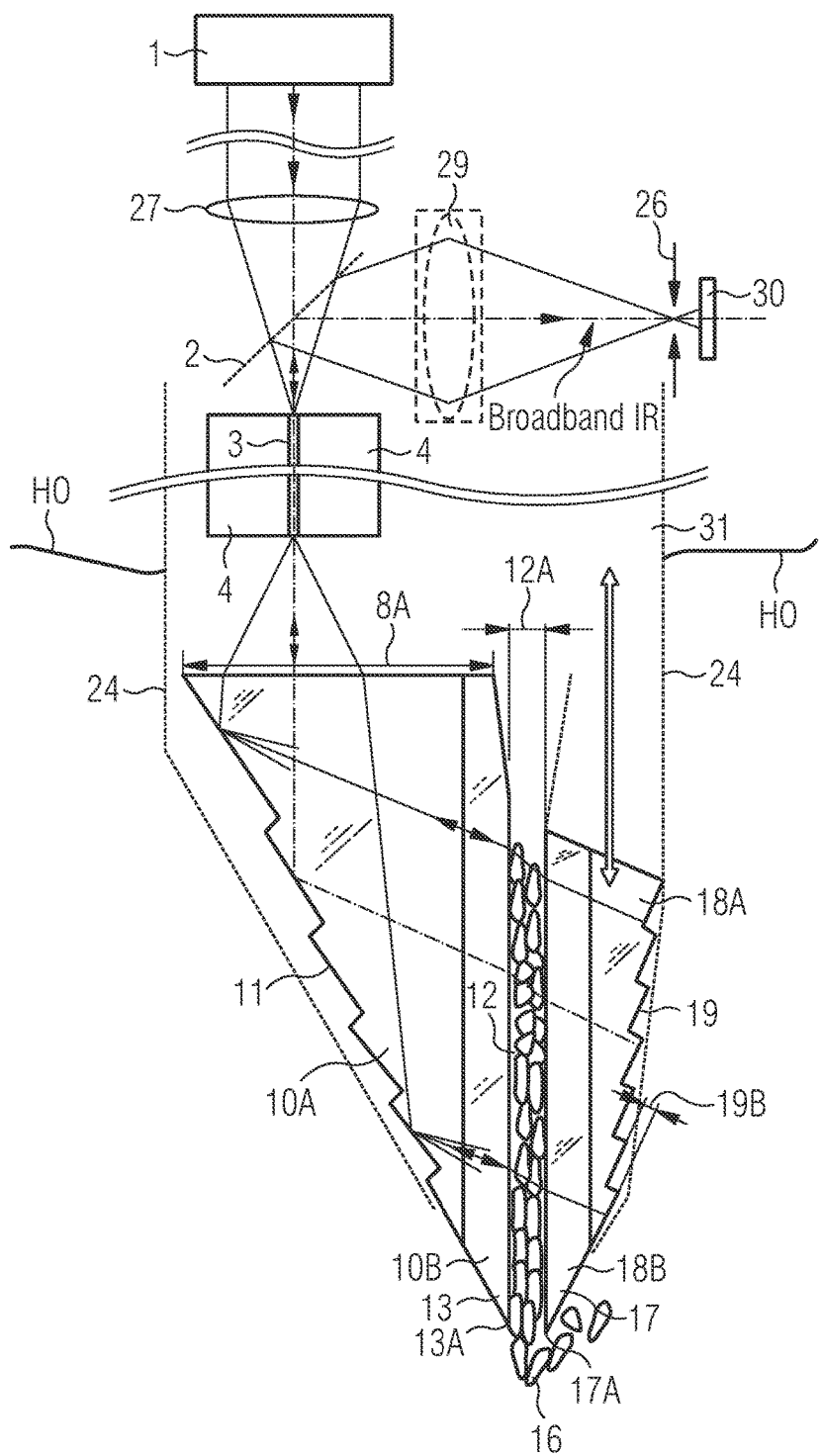

FIG. 19 shows a measuring probe according to a seventeenth example, and an arrangement for measuring spectral absorption comprising the measuring probe. The optical system of the measuring probe, or respectively the arrangement for measuring spectral absorption, shown in FIG. 19 substantially corresponds to the optical system of the measuring probe, or respectively the arrangement for measuring spectral absorption, shown in FIG. 17, with the difference that the measuring probe, or respectively the arrangement for measuring spectral absorption, comprises a fibre 4 (e.g., an MIR fibre) with a fibre core 3. The fibre can for example be a silver halide fibre. The fibre 4 is both a component of the illumination path as well as the detection path. Accordingly, the light source can be arranged at a somewhat greater distance from the measuring probe, such as for example in a position that is beneficial in terms of the design.

The light source can for example be a broadband or tunable light source. The optical system of the measuring probe is achromatised and designed such that the travelling measuring ray bundle is collimated after the compensation diffraction grating 11 (e.g., a blazed reflective diffraction grating) toward the end reflector 19 for the average wavelength within the broadband or tunable spectrum. After contacting the optical grating three times (once at the end reflector designed as a reflective diffraction grating, and twice at the compensation diffraction grating 11), the returning bundle preferably re-enters the fibre core 3 for all wavelengths in the broadband or tuned spectrum. All strong (harmful) reflections are hidden or blended out by a diaphragm (vignetting diaphragm) 26. Due to the comparatively small end reflector and the use of a fibre for the back and forth of the measuring light, additional installation space 31 is made available in order, for example, to arrange a microactuator system and positioning system for creating a cut-off tissue flap for the absorption measurement, or other components. Furthermore, installation space is provided by this arrangement for accommodating a channel for disposing of cut tissue after measurement, as needed.

In all of the above examples (see FIGS. 3 to 16), the measuring probe has a housing 24 in the form of a high-grade steel jacket which encapsulates the optical components. The diameter of the high-grade steel jacket 24 is for example 1.8 mm. During the measuring process, the width of the measuring gap is approximately 5 µm to 10 µm, such as 8 µm. The depicted measuring probes are in particular suitable for in vivo tissue measurements, such as during a surgical operation.

In the above examples, the measuring probe, or respectively the arrangement for measuring spectral absorption, can comprise a filter which is designed to filter out predetermined spectral bands from the broadband spectrum. Frequently the sought spectral signature is only found in a small number (e.g., 20) of absorption bands and their relationship with each other. The absorption bands relevant in a specific context can be known beforehand and saved in a database. In order to reduce the radiation load introduced while measuring absorption, only those spectral bands from which information is anticipated can be fed to the tissue by means of the filter to measure absorption (preferably with a certain spectral spread). The filter can for example comprise a frequency comb filter which basically only lets pass the spectral components relevant to measuring absorption, i.e., the spectral components which, with a certain probability, contain relevant absorption bands (for examples to diagnose cancer). The frequency comb filter can for example be designed as a dispersive spectrometer with a diffraction grating. Within the region of spectral separation of the dispersive frequency comb filter, highly reflecting and highly absorbing regions can be found, wherein the undesirable spectral components can be darkened by black, or respectively strongly absorbing regions. This can affect 80% or more of the intensity. The strongly reflected (desired, relevant) spectral components can be recombined in a focal point by means of diffraction in a diffraction grating and very efficiently coupled into a fibre (e.g., a monomode fibre).

With a Fourier approach (Fourier spectroscopy), a scanning two beam interferometer can be upstream or downstream from the frequency comb filter. Preferably, electromagnetic radiation, adapted by a priori knowledge, with a comb spectrum is supplied to the two beam interferometer. Preferably, the sample to be investigated (e.g., the tissue to be investigated) is arranged both after the frequency comb filter, as well as after the scanning two beam interferometer to minimize the radiation load. The radiation detector (as a part of the apparatus for spectral analysis) preferably follows the sample (e.g., the tissue) or respectively the measuring probe as closely as possible, in order to minimize signal loss and additional noise.

In the case of a light source with an addressable spectrum, lock-in detection can be performed for each of the relevant wavelengths, or respectively wavelength ranges (which correspond to the respective absorption bands). Since the number of absorption bands is low (e.g., 20) and their average wave number is generally known very precisely, a lock-in detection can be performed for this low number of addressed frequencies, or respectively frequency ranges.

If an MIR laser, or a battery of MIR lasers, is/are available as the light source and which covers or respectively cover the required absorption bands with a wavelength scan, the above described thinning of the broadband spectrum can be dispensed with. The spectral ranges irrelevant for diagnosing cancer can be left out of the scan, or passed through or scanned comparatively quickly.

The measuring results can be compared in real time with the spectral reference signatures, generated beforehand under comparatively similar conditions, of the sample to be investigated (e.g., the tissue to be investigated). The references signatures can for example be classified as benign, premalignant, malignant, or also more finely. The spectral reference signatures can for example be obtained by a lock-in detection. Preferably, an assignment, or respectively evaluation, of the freshly measured spectral signatures determined using the measuring probe is performed in real time or quasi-real time (e.g., under surgical conditions).

The detection process can comprise an accumulation of interferogram data as is known from the prior art. Preferably, the accumulation number (i.e., the number of accumulated interferograms) is n=1 since the probe is moving in the tissue (e.g. sliding into the tissue). A step-by-step mode is a prerequisite for accumulating interferogram data since otherwise optical data from different tissue sections are mixed in a single measurement.

For measurement, the tissue, or respectively the sample slice, preferably always remains within the measuring probe. During the measuring process, the measuring probe can be within the body of the patient (in vivo measurement). It is, however, possible to remove the probe for measuring tissue from the body of the patient and couple it into a measuring station, for example via a fibre port. In this case, the duration of measuring can increase (for example to a multiple of 10 seconds) to obtain improved lateral resolution. During this time, measuring can continue with a different probe in the patient. To this end, a supply in a cartridge can be provided on measuring probes. It is, however, possible to work simultaneously with a plurality of measuring probes and measure with them simultaneously at a port with several docking sites.

FIGS. 20 to 25 show examples of arrangements for the measurement of spectral absorption in a patient P, for example under surgical conditions. The arrangements for measuring absorption each comprise one light source such as a multi-wavelength light source having at least two wavelength ranges, a spectrally broadband light source, a wavelength-tunable source, and a light source with an addressable spectrum. The light source can furthermore comprise a filter 33 for filtering specific wavelength ranges, or respectively wavelengths. Likewise, the light source can comprise a light modulator for modulating specific wavelengths or wavelength ranges. The modulation can be temporal and/or spatial modulation.

Furthermore, the arrangements for measuring absorption comprise an apparatus for the spectral analysis of the signal coming from the measuring probe. The apparatus for spectral analysis comprises a detector 30, such as a cooled MCT detector. The arrangement for spectral absorption measurement can furthermore comprise an interferometer 35 (FIGS. 20 and 23 to 25), a spectrometer 43 (FIG. 21), a device for analysing signals over time (for example to analyse frequency over time), etc.

Figure 20:
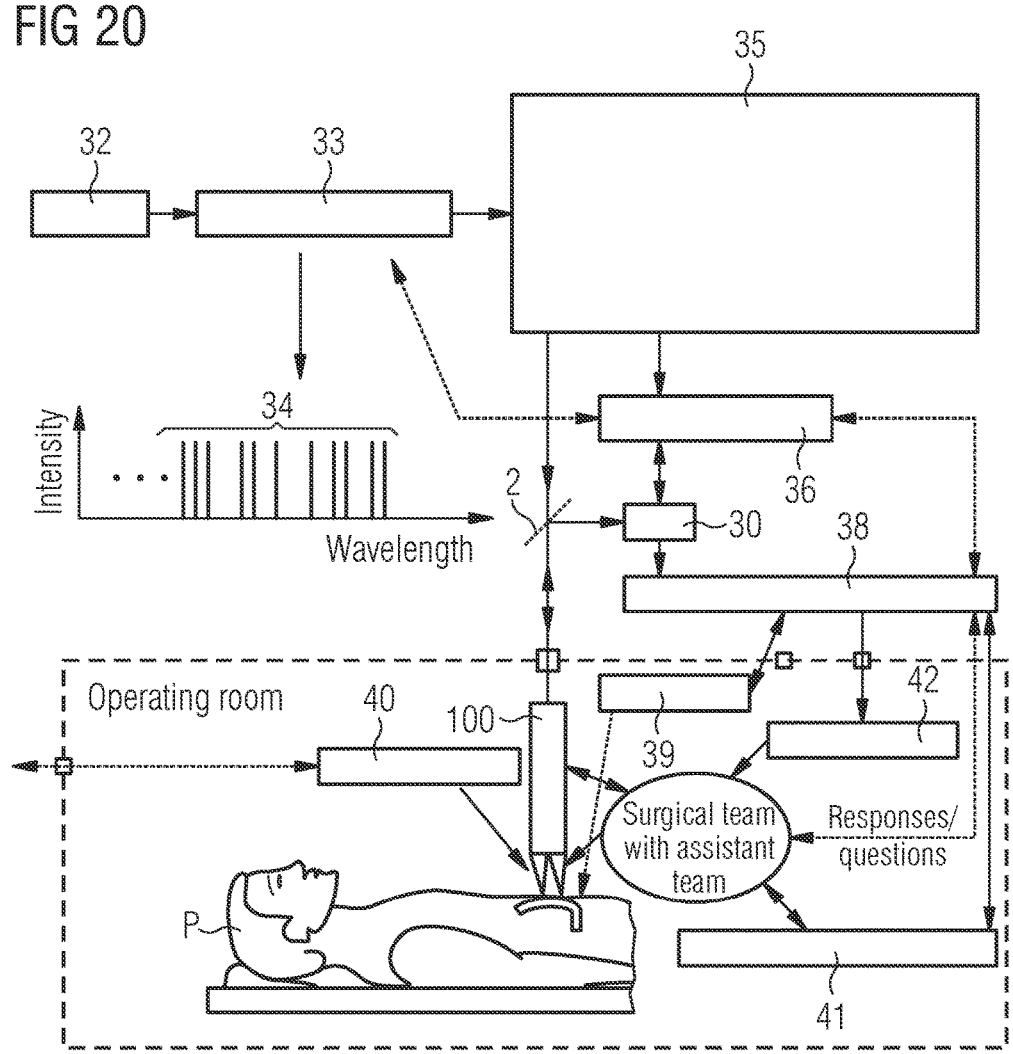
FIGS. 20 and 21 illustrate exemplary arrangements for measuring absorption in accordance with one or more aspects of the present disclosure.

The arrangement depicted in FIG. 20 for measuring spectral absorption comprises a broadband MIR source 32, a filter 33, and a two-beam interferometer 35 which is downstream from the filter 33.

As described above, the filter 33 can be designed to filter certain wavelength ranges, or respectively wavelengths which are relevant for obtaining information. The filter can for example be a filter with an adapted narrow-band pass filter characteristic. In one example, the filter can be specially created, or respectively configured for a specific patient, or respectively a specific application. Accordingly, the filter can be configured with previously obtained cancer patient data such as previously detected, sufficiently narrow absorption bands of cancerous and/or cancer-free tissue. The absorption bands can for example be determined by spectral measurement of areas which are unambiguously categorized as cancer-free and/or cancerous (for example by imaging methods and/or histopathological investigations). The data with which the filter is created, or respectively configured are preferably obtained soon before actual measurement (e.g., about 12 hours before a surgical operation in which the organs/tissue of the patient are to be measured).

The spectrum 34 of the illuminating light filtered and possibly modulated by the filter 33 consequently has a plurality of spectral ranges provided with intensity which are established according to previously determined data (e.g., cancer marker bands of the patient). Exclusively these bands, or respectively spectral ranges, are relevant as markers for obtaining information. This allows the radiation load from thermal radiation (MIR) to be significantly reduced to only 5 to 10% of the radiation load of unfiltered illuminating light. This minimizes the risk of burning the investigated sample (e.g., the investigated tissue) during the measuring process. The MIR source energy can then be elevated to the maximum tissue load which theoretically allows the cancer marker bands to be measured as quickly as possible without rapid tissue destruction (before the end of measurement). This however requires comparatively strong MIR laser sources.

The interferometer 35 can be a very fast and robust (ruggedized) two-beam interferometer which is vibration-resistant and stable over the long term. The interferometer can for example function according to the rotary reflector principle (double pendulum interferometer) with real-time FFT, or real-time lock-in evaluation. Examples of interferometers are for example known from DE3005520 A1, U.S. Pat. No. 4,383,762, DD210973A1, DE3400389A1, DE 42 12 143 A1 and GB2154019B as well as from the technical article by K. Körner, "Ein neues Interferometer für die Fourier-Spektroskopie" [A new interferometer for Fourier spectroscopy], Optik, vol. 68, p. 217-223 (1984).

The arrangement for measuring spectral absorption furthermore comprises a measuring probe 100 which for example can be one of the above-described measuring probes. A cartridge with measuring probes can furthermore be provided which has a large number (e.g., 16) of measuring probes. Accordingly after the measuring probe is used, the surgeon or surgical robot can insert a new sterile measuring probe to detect additional (possibly healthy) tissue areas. This is especially useful when several locations are to be optically scanned and there is a danger of infection, or contamination of healthy tissue by diseased tissue (e.g., cancer tissue cells) definitely should or must be excluded.

The filtered and possibly modulated light of the light source is coupled by the beam divider 2 into the measuring probe 100. By means of the beam divider 2, the measuring light is also conducted to the detector 30 after passing twice through the sample slice located in the measuring gap of the measuring probe.

For in vivo measuring, the measuring probe 100 is first introduced with or without the support of a surgical robot into the depth of the organ to be investigated, wherein the infeed direction of the measuring probe 100 substantially corresponds to the longitudinal axis of the measuring probe. Preferably, the measuring probe 100 is introduced supported by a robot arm into the organ, or respectively into the tissue of a patient P. The arrangement for measuring spectral absorption can accordingly be a device for introducing the measuring probe 41. The device can for example be a surgical robot, or can comprise a surgical robot. The puncturing by the measuring probe 100 while measuring preferably occurs at an at least approximately constant speed, such as 0.1 mm/s to 0.5 mm/s. If information on the tissue to be investigated is available, the areas of tissue which are already classified as "definitely healthy" can be quickly (e.g., at 5 mm/s) passed through (probe startup mode) since spectral measurement in these areas is unnecessary.

The position of the measuring probe 100 with reference to the investigated organ can be determined using previously obtained or ascertained data with reference to the spatial orientation of the patient's body and/or the investigated organ. In addition, the position of the measuring probe in the investigated organ can be measured using suitable measuring procedures (e.g., CT, ultrasound, microscope, etc.), preferably in real time, and depicted on a suitable display (such as a screen 40). With reference to the data on the position of measuring probe, the measuring process can be started. The arrangement for measuring spectral absorption can accordingly comprise a device for 3-D localization 39 of the position of the measuring probe with respect to the investigated sample (e.g., with respect to the investigated organ).

In addition to the detected data with respect to the position of the measuring probe 100, the global shape of the body (body displacements) of the patient can be measured, for example by means of fast 3-D strip projection measuring. The detected 3-D data can be used for active patient fixation. Previously installed reference points of the patient's body (marks) can for example be positionally stabilized with reference to the robot arm by a surgical table system.

The detected measuring light is spectrally evaluated with a control and/or processing system 38. The control and/or processing system 38 can comprise a database in which reference spectra are saved. The reference spectra can be used when analysing the detected measuring data and/or when adapting the filter 33.

The reference spectra can be determined by statistical investigations. Preferably, the reference spectra can be determined in investigations of the specific patient, preferably soon before a surgical operation. The reference spectra can for example be determined by taking a biopsy followed by a spectral measurement. One reason is that the cellular metabolism within the human body is sometimes subject to large fluctuations, for example due to rapid inflammatory processes in the body, the dynamics of the water and nutritional metabolism, chronic metabolic diseases such as diabetes, or ulcerative colitis, the hormone status, especially in women, special medications, etc. Preferably, tissue samples (e.g., in vivo) are spectrally measured and histopathologically evaluated in an (initial small) surgical diagnostic operation or investigation (DOP) in the surgical area. Preferably, the measurement is performed within a period of less than 24 hours, or preferably less than 12 hours, before the actual surgical operation. The histopathologically determined features are for example divided by a histopathologist into classes (e.g., benign, premalignant, malignant, or optionally more fine classes) and assigned to the respectively measured spectra. The features, or respectively classes, and the reference spectra are saved in the patient database. The saved reference spectra and classification can be automatically retrieved, or retrieved by a surgeon, or respectively a surgical team.

In a subsequent, large surgical operation (SOP), the spectra are obtained by the measuring probe, or respectively arrangement for measuring spectral absorption, of previously uninvestigated tissue samples which are freely accessible mechanically and possibly also visible for the first time to the surgeon. By comparing with the saved patient-related reference spectra (which was obtained in the DOP), an evaluation of the tissue material measured during the SOP can be performed. Known methods of statistical mathematics such as correlation techniques, PCA, hierarchical methods, etc. can be used for the spectral analysis.

In another approach, a cancer tumour or another pathological tissue change in the patient can be unambiguously diagnosed before the SOP. This diagnosis can for example be performed in an imaging procedure and histopathological investigation. By femtosecond flashes within the infrared spectral range (preferably at the 3 µm wavelength), tissue which has been cut out can be heated, dehydrated and/or evaporated in the measuring probe (e.g., a small volume of the cutout tissue at the tip of the measuring probe, or respectively in the measuring gap). Then the tissue to be evaporated (vaporized) can be analysed time-resolved with a dispersive single shot spectrometer, or another suitable spectrometer, following the measuring probe within the MIR spectral range (e.g., within a range of 7 µm to 11 µm). In particular, the cut-out tissue in the measuring probe can be illuminated with MIR radiation for spectroscopic analysis so that the radiation with a high spatial coherence emitted by the vaporized tissue can be optimally coupled into the gap of the dispersive single shot spectrometer. The femtosecond flashes and MIR radiation can be transmitted at a delay, wherein the spectrometer is preferably protected from femtosecond flashes (for example by a controllable optical shutter). Reference spectra can be obtained using this procedure. It is likewise possible to use this procedure when obtaining spectral data from previously uninvestigated tissue samples in the SOP.

With reference to the obtained spectral data during the SOP, a 2-D or 3-D map 42 of the investigated tissue, such as a 2-D or 3-D tumour map, can be created. The 3-D map 42 can be displayed in real time.

For the operation, a detailed schedule for the measuring probe movement can be worked out beforehand and saved in a computer system (e.g., a processing system 38) for a surgical robot. Depending on the situation, the plan for moving the measuring probe can preferably be altered relatively quickly, and new incision lines for removing tissue can accordingly be proposed, or respectively calculated, during surgery using the probe data and possibly other data and information (e.g., the visual impression of the surgeon, the camera data, scan findings, the general situation of the patient, the patient's endurance during surgery, and the circulatory situation).

The control and/or processing system 38 can be linked by a signal connection to a device control unit 36. The device control unit can for example regulate and/or control the filter 33, the interferometer 35 and/or other optical and/or mechanical components of the arrangement for spectrally measuring absorption. The device control unit 36 can be designed as a component of the control and/or processing system 38, or as a separate module.

Figure 21:
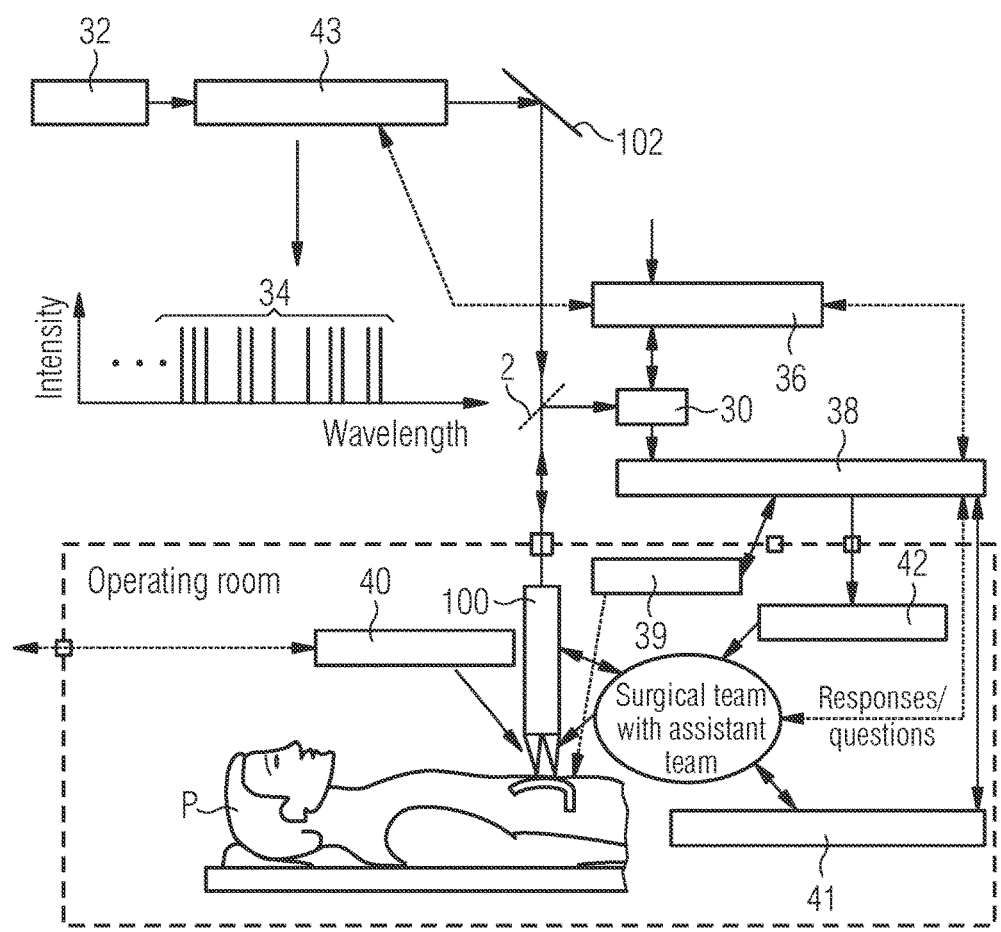

FIG. 21 shows another exemplary arrangement for measuring spectral absorption. The design and components of the arrangement for measuring spectral absorption largely correspond to the design and components of the arrangement shown in FIG. 20, with the difference that the arrangement comprises a spectrometer 43. The spectrometer 43 can be an SLM grating spectrometer with a selective frequency spread. The spectrometer 43 can furthermore have a filter with a narrow band pass filter characteristic as described in conjunction with FIG. 20. The (modulated) measuring light is coupled into the measuring probe 100 via the deflection mirror 102 and the beam divider 2.

Figure 22:
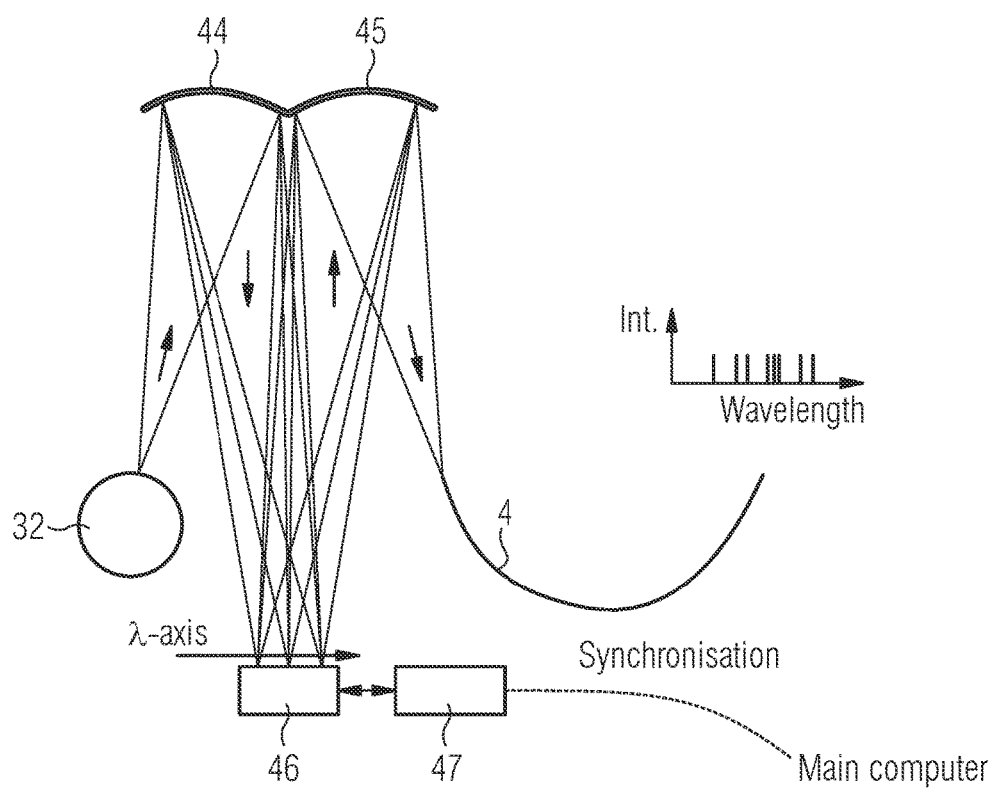
FIG. 22 illustrates an exemplary light source with an addressable spectrum in accordance with one or more aspects of the present disclosure.

In the above examples, the light source can be a light source (e.g., a light source in the MIR) with an addressed spectrum. FIG. 22 shows an example of a light source with an addressed, or respectively addressable spectrum. The light source comprises a broadband light source 32 with a continuous or discrete spectrum (e.g., a brilliant broadband light source). By means of a first diffraction grating 44, the different spectral components of the spectrum are spatially separated from each other and depicted on a spatial light modulator 46, wherein the individual structural components contact different areas of the spatial light modulator. The spatial light modulator can for example be an addressed digital micromirror device with a gold mirror coating on the micromirror elements for the narrow band pass filter. Other spatial light modulators (e.g., LCDs) can also be used. The individual spectral components are time modulated by the spatial light modulator 46, wherein the modulation frequencies of the individual spectral components are different from each other. The spatial light modulator is controlled, or respectively regulated by an apparatus for controlling frequency 47.

By means of a second diffraction grating 45, the individual modulated spectral components are combined and coupled into the fibre 4. The spectrum of the light generated by the broadband light source 32 consequently has a plurality of spectral components that for example are each time-modulated with different frequencies. The spectral components detected by a detector (e.g., a two-dimensional detector) can be separated using temporal Fourier analysis, wavelet analysis or another frequency analysis. A suitable device for spectral analysis comprising a light source with an addressed spectrum is for example described in German patent application DE 10 2014 002 514.4 to which reference is made.

FIG. 23 shows another exemplary arrangement for measuring spectral absorption. The arrangement comprises a brilliant source 32 (such as a brilliant synchrotron source or a laser package, preferably within the MIR range), a device for spectral separation 49, preferably by means of diffraction, a mask or a device for static light modulation 50 (e.g., a filter), a device for spatial spectral combination 51 of the spatially separate spectral components (for example by means of diffraction), an interferometer 53 (e.g., a Michelson interferometer), as well as optional fibres, or respectively optical waveguides 52 and 4 (e.g., a monomode fibre). The device for static light modulation 50 can, as described above, serve to thin out the broadband spectrum of the source 32 and for example comprise a spatial light modulator, such as a reflective SLM. The arrangement for measuring spectral absorption furthermore comprises a measuring probe 100 (e.g., one of the above-described measuring probes) a detector 30, and a control and/or processing system 38. The functioning of this arrangement is similar to the arrangement shown in FIG. 20.

FIG. 24 shows another exemplary arrangement for measuring spectral absorption. The arrangement comprises a light source with an addressable spectrum such as the light source shown in FIG. 22. The light source comprises a brilliant source 32 (e.g., a brilliant synchrotron source or a laser package, preferably within the MIR range), a device for spectral separation 49, for example by means of diffraction, a device for dynamic light modulation 55, a device for spatial spectral combination 51 of the spatially separate and modulated spectral components (preferably by means of diffraction), and an interferometer 53 (e.g., a Michelson interferometer). The spectrum addressable with light can optionally be coupled into a fibre 4 (e.g., a monomode fibre) and fed to the measuring probe 100. The device for dynamic light modulation 55 can for example comprise a reflective SLM and address the spectrum of the broadband source 32 as described above. Optionally, the device for dynamic light modulation 55 can also be designed for the predetermined thinning out of the spectrum. The arrangement for measuring spectral absorption furthermore comprises a detector 30 and a control and/or processing system 38 which is designed to perform a frequency analysis of the detected measuring signal. The functioning of this arrangement is similar to the arrangement shown in FIG. 20.

Figure 25:
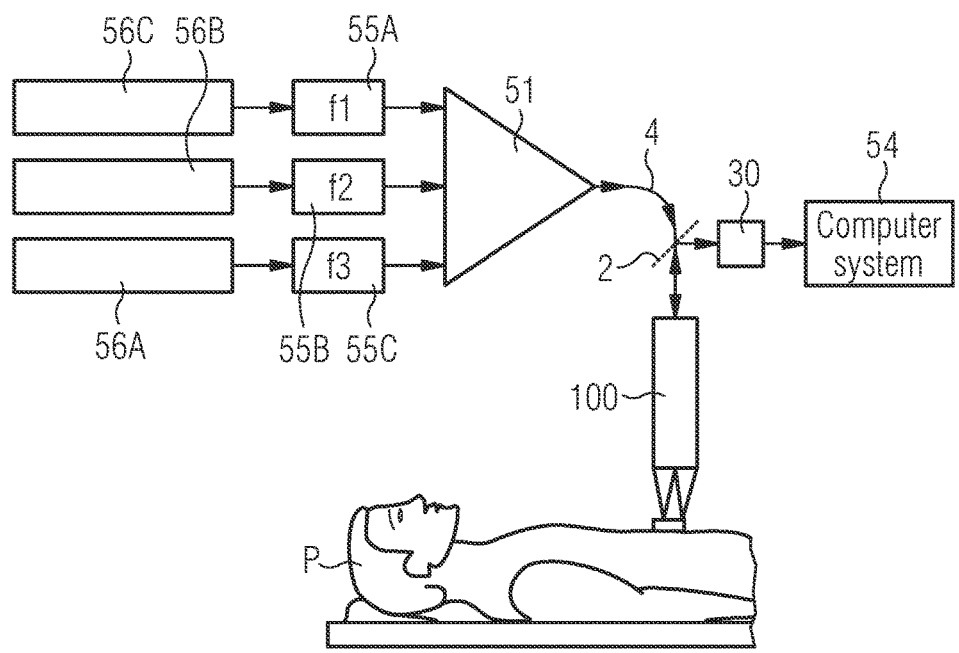

FIG. 25 shows another exemplary arrangement of measuring spectral absorption with a light source with an adjustable spectrum. The light source with the addressable spectrum comprises a plurality of monochromatic light sources 56A, 56B and 56C, such as three lasers with wavelengths of 1084 cm$^{-1}$, 1235 cm$^{-1}$ and 1650 cm$^{-1}$, respectively. A separate modulation device 55A-C is assigned to each of the light sources 56A-C and is designed to modulate the light of the respective light sources 56A-C over time with their own respective frequency of f1, f2, f3. By means of the device for spatial spectral combination 51, the individual modulated monochromatic light rays are combined, for example by means of diffraction, and coupled via a fibre 4 into the measuring probe 100. The arrangement for measuring spectral absorption furthermore comprises a detector 30 and a control and/or processing system 38 which is designed to perform a frequency analysis of the detected measuring signal. The functioning of this arrangement is similar to the arrangement shown in FIG. 20.

In the above examples, the analysis of the detected data can comprise a main axis transformation (PCA, principal component analysis) for obtaining spectral features from the investigated sample. The numeric method of the PCA can follow the spectroscopic analysis as a numeric selective tool. Spectra can be used that are saved in databases and whose spectral features are assigned to the substances to be searched. Other numeric methods are also possible.

The combination of Fourier transformation spectroscopy and PCA or other numeric tools requires that the spectra to be provided have, or respectively do not fall below, a minimum spectral resolution in order to obtain sharp features. This ensures that the measured sample will be reliably identified and classified. Furthermore, the spectral data may not fall below a minimum signal/noise ratio so as not to endanger the reliability of the information. The investigated tissue (e.g., cancerous tissue, healthy tissue, possibly with immediate levels) can be classified on the basis of the analysis. The measured sample is preferably classified in real-time or quasi-real time. This allows for example a surgeon to be effectively supported in the decision as to whether and to what extent a still-operable tumorous lesion can be removed. In particular, the location of incision lines for the surgeon in the submillimeter range can be supported by the proposed measuring probes, as well as the arrangement and method for measuring spectral absorption. The obtained data can also be used in a preliminary investigation under general/local anaesthesia.

The spectral recording time per measuring site in measuring mode is preferably approximately 1 s to 10 s, and also up to 100 s in a few instances. Shorter spectral recording times are also possible. A certain amount of lateral smearing of the recording sites for spectral data from the measuring probe sliding during measurement can be acceptable as the case may be. It is possible to perform the measurement in a step-by-step mode to achieve high lateral (local) resolution. The overall recording time correspondingly lengthens, however.

The spatial/local resolution of the measurement preferably lies within a range of 0.05 mm to 1 mm, preferably 0.1 mm to 0.3 mm. Accordingly for example, a locally/spatially resolved spectral signature can be created across the tissue or along a relevant tissue channel to be defined. Since the measuring probe can be designed in the form of a low-volume, comparatively thin needle, or respectively a probe, it is possible to perform an in-vivo tissue diagnosis and create complete tissue depth profiles. This can for example promote a comparatively fast performance of a surgical operation with minimal loss of healthy organ soft tissue of the patient by determining the preferably three-dimensional incision lines in soft tissue which are optimum from a medical standpoint. This allows precise planning of surgery, or data-supported adaptation of surgery in real time. The surgery can be performed using the data obtained from measuring spectral absorption (possibly in combination with other data) for example with the assistance of a robot arm.

The measuring probe, or respectively the arrangement for measuring spectral absorption, can furthermore be combined with other devices for detecting data such as OCT probes, RAMAN probes, etc. In particular, the data obtained by measuring spectral absorption can be used directly (for example to obtain information on the nature of the sample), or combined with available data from measurements of another type (such as image processing microscopy in UV, VIS or NIR, including phase contrast microscopy, fluorescence spectroscopy in NIR, Raman spectroscopy, NIR scattered light spectroscopy, CT, PET and MRT) so that a multivariate data set can be formed, preferably in real time or quasi-real-time. By using this data set, reliable decisions can for example be made by a surgeon on whether to perform a surgery under surgical conditions.

Uses of the measuring probe and the arrangement and method for measuring spectral absorption comprise, for example, the discernment of tumours or complex in vivo metabolic processes for example during the surgical operation phase, and/or in the administration of medications (time-resolved reaction kinetics). Other uses comprise the quick and reliable identification of previously known (e.g., hazardous or forbidden) organic substances in a highly complex situation in biological or technical soft tissue (in vivo, ex vivo). The presence of certain organic substances (such as drug residues, organic poisons in homicides, drugs in sports, undeclared or forbidden additives in meat for consumption, etc.) can for example be reliably confirmed quantitatively by molecular spectroscopy or excluded within the given measuring resolution.

Applications within the technical field are also possible, such as measurement in soft plastics and/or plants.

Another exemplary method for measuring spectral absorption comprises the following steps:

In a medical investigation, a thin flap of tissue, or respectively a thin tissue slice (sample slice) of an at least approximately constant thickness is created, including in the depth of the tissue (possibly centimeters deep), for diagnostic purposes directly in an optical arrangement for measuring spectral absorption.

The thin tissue flap is transilluminated to measure the absorption spectra of biomolecules for diagnostic purposes directly in the tissue. The used radiation is preferably a spectral range within the medium infrared.

In the arrangement, the created thin tissue flap (with its large surfaces) is:
either bordered by two at least approximately flat window surfaces (end reflector in the background, wherein the end reflector can then be a flat mirror); or
bordered by an approximately flat window surface (assigned to the primary blade) and an end reflector (designed as a micro-profiled (blazed) reflective grating).

A parallel bundle or a weakly focused bundle is used which contacts the end reflector and is continuously reflected there. In the process, the one or two at least approximately flat window surfaces are transilluminated at an angle—at such an angle that no part of the light directly reflected by the window surfaces can take the same path back toward the light source.

The thin tissue flap is transilluminated a first time to generate absorption at that location. The light then reaches the end reflector. After the reflection at the end reflector, the thin tissue flap is transilluminated a second time to again generate absorption therein (producing amplification of the measuring effect).

After passing twice through the tissue flap, the light reflected by the end reflector may either return at least approximately into itself where it is subsequently coupled out in the detection channel by beam division, or it propagates in a detection channel separate from the input bundled ray path.

The end reflector in the background, preferably designed as a flat mirror, is at an angle relative to the flat window surface of the primary blade. This prevents an undesirable recordable channelled spectrum, or at least its effect which distorts the measuring results.

The parallel bundle can for example originate from a laser, a quantum cascade laser in MIR. The quantum cascade laser is preferably designed with a tunable wavelength. Alternatively, the laser can be designed as an IR broadband laser in conjunction with a spectrometer.

The thin tissue flap is preferably created by mechanical dissection with sharp blades. In relation to its limited thickness, the thin tissue flap has two comparatively extensive boundary surfaces. These either lie against the two windows, or against one window and the end mirror. Preferably, each boundary surface of the thin tissue flap is created by dissection with its own blade. The two extensive boundary surfaces are preferably created by mechanical dissection.

The primary blade of the measuring probe always penetrates as the first blade into deeper tissue sections during a medical investigation when approaching the diagnostic target area. The secondary blade can move relative to the primary blade. The secondary blade is always held back, however, and is never in front of the primary blade. Reason: The secondary blade can be smaller and weaker.

The secondary blade can preferably also move in an up-and-down movement relative to the primary blade. This can strongly favour the creation of a very thin tissue flap. This oscillating movement can have a small, high-frequency oscillating amplitude. The mechanical dissection process of the secondary blade is preferably supported by vibration within the ultrasonic range.

The advancement of a movement by a blade can be preferably a least one-half the length of the lateral scanning range during measurement. In the process, the length of the scanning range determines the spatial/local resolution of the measuring probe.

Another exemplary arrangement for measuring spectral absorption has the following features:

The spectrometric arrangement can for example comprise a broadband source and a spectrometer, or a wavelength-tunable source and a detector, and at least one measuring probe having optical contact with the tissue which is transilluminated by light. The wavelength-tunable source is preferably a quantum cascade laser in the medium IR.

In the measuring probe, there is a primary and secondary blade for dissecting tissue to create a comparatively thin tissue flap. The thin tissue flap can for example possess a thickness between 1 µm and 30 µm, typically 4 µm to 12 µm, for measurements in the medium infrared.

The problem of the undesirable channelled spectrum which is caused in this exemplary arrangement, for example, by multiple reflections within the nearly parallel measuring gap is counteracted on the one hand by not-too-slight absorption in the tissue flap due to the chosen flap thickness. Furthermore, direct reflections on the window surfaces in this arrangement with at least approximately flat window surfaces arise from window surfaces transilluminated at an angle, and therefore the individual reflections on these surfaces tend to be unable to generate an undesirable channelled spectrum. However, an undesirable partial bundle pair generated by a zigzag reflection on the window surfaces can coherently overlap the measuring bundle since it possesses the same direction of propagation in the parallel gap. When the undesirable partial bundle is even slightly tilted relative to the measuring bundle, this effect of the undesirable channelled spectrum is further attenuated. This requires a somewhat wedged-shaped measuring gap. The optimum tilting angle can be quantitatively determined as follows: Approximately one-half the average wavelength over the effective measuring length in order to arrive at the first zero position of the interference modulation by means of the integration effect over the measuring surface. In the case of an aqueous medium, a change in the wedge thickness of 3 µm to 4 µm along the measuring length (gap height/gap length) is sufficient. However, due to the wedge-shaped tissue flap, the absorption significantly depends on the location of the measuring gap, which is not optimum. The measuring field is therefore weighted.

Furthermore, an anti-reflective coating on the window surfaces can help significantly to reduce the effect of the undesirable channelled spectrum. For diamonds, however, there is no anti-reflective coating which can be used. Calculation can be useful in this context (e.g., the numerical differentiation of the spectral data). Given the small gap which means only a few wavelengths of optical path difference (OPD) for the effect of the undesirable channelled spectrum, this constitutes rather long-period modulations over the wave number in any case.

In this example, the primary and secondary blade made of transparent material in the IR range, or are fixedly connected to components made of transparent material in the IR range (along the shortest path in optical contact). The primary blade piece is preferably assigned an optical window surface. The secondary blade is preferably assigned either an optical window surface with a rear mirror or only a front end mirror (blazed reflection grating). During the measuring process, a part of the least partially cut-off tissue flap, or individual tissue pieces, lies or lie on each window surface.

Optical contact is established with the tissue flap through the optical windows surfaces. These optical window surfaces are at least approximately parallel.

The primary blade is preferably a part of a prism with a light entry surface (primary blade prism). The end reflector is assigned to the secondary blade. The end reflector can for example be designed as a flat mirror (in that case as a rear mirror), or as a rooftop mirror prism (in that case as a rear mirror), or as a micro-profiled reflective grating (in that case as a blazed front mirror). The optical window surface on the primary blade prism either encloses preferably a sharp angle with the longitudinal axis La of the measuring probe, or the optical window surface is preferably parallel to the longitudinal axis La of the measuring probe. Furthermore, the light entry surface on the primary blade prism is preferably at a slight angle so that reflections on said primary blade prism are (largely) blocked by the diaphragm (vignetting diaphragm) in the detection ray path.

Furthermore, in the detection channel and outside of the measuring probe in front of the detector, there is a focusing optical system with a fine diaphragm (vignetting diaphragm) located in the focal path of the fine diaphragm in order to hide or blend out the (numerous strong) undesirable reflection spots. This holds true in particular when a laser is used (e.g., a QCL). The fine diaphragm is preferably designed as a slit diaphragm.

The secondary blade is designed to be finely adjustable relative to the primary blade. For a fine, highly-precise and low-friction adjustment of the secondary blade, an aerostatic micro-bearing is integrated in the measuring probe which bears the secondary blade. For this purpose, the measuring probe is supplied with (purified) compressed air. The micro-oscillations to improve the effect of cutting the tissue (preferably also within the ultrasonic range) preferably act on the secondary blade, on the primary blade and/or on the measuring probe.

Preferably, a coupling-out beam divider is arranged in the detection ray path for coupling out the light after passing twice through the tissue flap. The coupling-out beam divider is downstream from a diaphragm (vignetting diaphragm).

If the end reflector is designed as a reflective diffraction grating, a compensation diffraction grating is preferably arranged to at least approximately achromatise the optical system until detection. This is associated with greater efficiency of the IR measurement radiation and the suppression of interfering light (reflection) in the detection channel.

The blazed compensation diffraction grating is preferably arranged on the primary blade piece. Since diamond is very difficult to microprofile, a combination with a zinc selenide piece, which is easy to produce, is recommendable, even computer-controlled by means of diamond processing. The zinc selenide piece has the blazed compensation diffraction grating. The zinc selenide piece is connected to a diamond blade piece.

Furthermore, there can be auxiliary blades (not shown) which cut off the tissue flap even on the narrow sides so that it can be removed "upwards" (to the outside). The cut-off tissue removed from the body after measuring can serve for additional external medical investigation (in histology).

TABLE I

List of Reference Numerals with Descriptors:

| Reference Numeral | Description |
|---|---|
| 1 | Light source for IR spectroscopy |
| 2 | Beam divider or splitter (coupling-in and coupling-out beam divider) |
| 3 | Fibre, or respectively optical waveguide core |

TABLE I-continued

List of Reference Numerals with Descriptors:

| Reference Numeral | Description |
|---|---|
| 4, 4A, 4B | Optical waveguide, or respectively fibre (e.g., an MIR fibre) |
| 4A | Transmission, or respectively illumination fibre, or respectively waveguide |
| 4B | Detection fibre, or respectively waveguide |
| 5, 5A, 5B | Fibre core end |
| 6, 6A, 6B | Lens (e.g., an aspherical lens) |
| 7 | Free-form surface of the aspherical lens |
| 8 | Entry surface of the window element |
| 8A | Width of the entry surface |
| 9 | Window surface |
| 10 | Window element |
| 10A, 10B | Component of the window element |
| 11 | Compensation diffraction grating |
| 12 | Measuring gap |
| 12A | Width of the measuring gap |
| 13 | First cutting blade (primary blade) |
| 13A | Blade edge, or respectively tip |
| 14 | Sample entry |
| 15 | Mirror |
| 16 | Sample (e.g., a tissue sample, or respectively tissue) |
| 16a | Aqueous medium |
| 16b | Sample particle (e.g., a tissue particle) |
| 17 | Second cutting blade (secondary blade) |
| 17A | Blade or cutting edge, or respectively tip |
| 18 | End reflector support element (e.g., a hard metal or diamond body) |
| 18A, 18B | Component of the end reflector support element |
| 19 | End reflector |
| 19A | Grating period |
| 19B | Grating height |
| 20 | Output of the measuring channel (sample outlet) |
| 21 | Removal channel (discharge or disposal channel) |
| 22 | Apparatus for spectral analysis |
| 23 | Light modulator (e.g., a Michelson interferometer) |
| 24 | Housing |
| 25 | Window surface of the end reflector support element |
| 26 | Auxiliary diaphragm or aperture |
| 27 | Ray-forming optical system |
| 28 | Deflection optics (e.g., a deflection mirror) |
| 29 | Focusing optical system |
| 30 | Detector |
| 31 | Installation space (e.g., for a positioning system for the end reflector support) |
| 32 | Broadband light source |
| 33 | Filter |
| 34 | Modulated light spectrum |
| 35 | Two ray interferometer |
| 36 | Apparatus control unit |
| 38 | Control and/or processing system |
| 39 | Device for 3-D localization |
| 40 | Screen |
| 41 | Device for introducing the measuring probe |
| 42 | 3-D map |
| 43 | Spectrometer |
| 44, 45 | Diffraction grating |
| 46 | Spatial light modulator |
| 47 | Device for controlling frequency |
| 48, 52 | Optical waveguide |
| 49 | Device for spectral separation |
| 50 | Device for static light modulation |
| 51 | Device for spatial spectral combination |
| 53 | Interferometer (e.g., a Michelson interferometer) |
| 54 | Computer system for spectral analysis |
| 55, 55A-C | Device for dynamic light modulation |
| 56A-C | Monochromatic or quasi-monochromatic light sources |
| 100 | Measuring probe |
| 102 | Deflection mirror |
| La | Longitudinal axis of the arrangement for measuring absorption (Z-axis) |
| V | Infeed direction (direction of movement of the measuring probe) |
| T | Sample transport direction (e.g., the tissue transport direction) |

TABLE I-continued

List of Reference Numerals with Descriptors:

| Reference Numeral | Description |
| --- | --- |
| MV | Microvibrations |
| S | Measuring ray (preferably collimated) |
| BO | Order of diffraction |
| P | Patient |
| HO | Skin surface |

We claim:

1. A measuring probe for measuring spectral absorption, comprising
a cutting apparatus configured to cut off a sample slice of a sample to be measured, wherein the cutting apparatus comprises a first cutting blade and a second cutting blade, wherein the second cutting blade is configured to be movable relative to the first cutting blade;
a measuring gap configured to accommodate the sample slice;
an optical window element for coupling measuring light into, or respectively out of the measuring gap, such that the sample slice endures at least a first transillumination; and
an end reflector configured to reflect the measuring light propagated through the measuring gap back into the measuring gap.

2. The measuring probe according to claim 1, wherein at least one of the first cutting blade or the second cutting blade is connected to at least one of an optical window element and an end reflector support element.

3. The measuring probe according to claim 1, wherein at least one of the first cutting blade or the second cutting blade includes at least one of a cutting tip and a cutting edge with an angle less than 90°.

4. The measuring probe according to claim 1, wherein at least one of the first cutting blade or the second cutting blade is made of a material transparent to the measuring light.

5. The measuring probe according to claim 1, wherein the measuring gap has a variable width.

6. The measuring probe according to claim 1, wherein the measuring probe has an elongated shape with a longitudinal axis, and wherein the measuring gap is arranged at an angle to the longitudinal axis of the measuring probe, wherein the angle between a longitudinal direction of the measuring gap and the longitudinal axis of the measuring probe is preferably from 3° to 70°.

7. The measuring probe according to claim 1, wherein the measuring probe has an elongated shape with a longitudinal axis, and wherein the measuring gap is arranged substantially parallel to the longitudinal axis.

8. The measuring probe according to claim 1, wherein the end reflector comprises a retroreflector.

9. The measuring probe according to claim 1, wherein the measuring probe comprises at least one compensation diffraction grating configured to at least approximately achromatise an optical system of the measuring probe.

10. The measuring probe according to claim 1, wherein the measuring probe is arranged such that an incidence of the measuring light at refractive optical surfaces of the measuring probe is not perpendicular.

11. The measuring probe according to claim 1, wherein the end reflector forms at least a first surface bordering the measuring gap.

12. The measuring probe according to claim 1, wherein the end reflector is arranged at an angle to a window surface of the window element, wherein the window surface is configured such that the measuring light is coupled into the measuring gap and out of the measuring gap through the window surface.

13. The measuring probe according to claim 1, wherein the measuring probe comprises at least one spectral filter configured to filter out predetermined spectral bands from a spectrum comprising a plurality of wavelengths.

14. A method for measuring spectral absorption, comprising
accommodating a sample slice in a measuring gap of a measuring probe;
dehydrating the sample slice;
coupling-in measuring light into the measuring gap through a window element such that the sample slice endures a first transillumination;
reflecting the measuring light at an end reflector back into the measuring gap such that the sample slice endures a second transillumination;
coupling-out the measuring light, wherein the measuring light was propagated twice through the sample slice, and out of the measuring gap through the window element; and
detecting at least part of the coupled-out measuring light.

15. The measuring probe according to claim 1, wherein the end reflector is arranged parallel to a window surface of the window element, wherein the window surface is configured such that the measuring light is coupled into the measuring gap and out of the measuring gap through the window surface.

16. A system for measuring spectral absorption, comprising:
a measuring probe, the measuring probe comprising:
a cutting apparatus configured to cut off a sample slice of a sample to be measured, wherein the cutting apparatus comprises a first cutting blade and a second cutting blade, wherein the second cutting blade is configured to be movable relative to the first cutting blade;
a measuring gap configured to accommodate the sample slice;
an optical window element for coupling measuring light into, or respectively out of the measuring gap, such that the sample slice endures at least a first transillumination; and
an end reflector configured to reflect the measuring light propagated through the measuring gap back into the measuring gap; a light source, wherein the light source is at least one of: a spectral broad-band light source, a multiwavelength light source, a light source with tunable wavelengths, and a light source with an addressable spectrum; and
an apparatus configured to perform a spectral analysis of the measuring light coupled out of the measuring gap.

17. The method according to claim 14, wherein after being coupled out of the measuring gap, the measuring light is coupled into a detection channel separate from an input bundle ray path.

18. The method according to claim 14, wherein after being coupled out of the measuring gap, the measuring light at least approximately returns back into itself and is then coupled into a detection channel.

19. The method according to claim 14, further comprising:
compressing the sample slice; and
filtering a broadband spectral light emitted by a light source in order to let through predetermined spectral ranges, wherein the measuring light is within the predetermined spectral ranges.

20. The method according to claim 14, further comprising:
filtering a broadband spectral light emitted by a light source in order to let through predetermined spectral ranges, wherein the measuring light is within the predetermined spectral ranges.

* * * * *